US006245560B1

(12) United States Patent
Lisziewicz

(10) Patent No.: US 6,245,560 B1
(45) Date of Patent: Jun. 12, 2001

(54) VECTOR WITH MULTIPLE TARGET RESPONSE ELEMENTS AFFECTING GENE EXPRESSION

(75) Inventor: Julianna Lisziewicz, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/245,506

(22) Filed: May 18, 1994

Related U.S. Application Data

(63) Continuation-in-part of application No. 08/069,476, filed on Jun. 1, 1993, now abandoned, which is a continuation of application No. 07/596,299, filed on Oct. 15, 1990, now abandoned, which is a continuation-in-part of application No. 07/467,407, filed on Jan. 18, 1990, now abandoned.

(51) Int. Cl.$^7$ .................................................... C12N 15/00

(52) U.S. Cl. ...................... 435/320.1; 536/23.1; 536/24.1

(58) Field of Search ............................. 435/320.1, 240.1, 435/240.2, 325; 424/93.21, 93.2

(56) References Cited

U.S. PATENT DOCUMENTS 5,837,510 * 11/1998 Goldsmith et al. ............... 435/172.5
5,861,290 * 1/1999 Goldsmith et al. ................. 424/93.2

FOREIGN PATENT DOCUMENTS

B-18848/88 1/1989 (AU) .
0594881 5/1994 (EP) .
WO 90/07936 * 7/1990 (WO) .
WO91/10453 7/1991 (WO) .

OTHER PUBLICATIONS

Baltimore, D. *Nature*, Intracellular immunization, 335:395–396 (1988).

Cotten, et al. *EMBO Journal*, Ribozyme mediated destruction of RNA in vivo, vol. 8, No. 12, pp. 3861–3866 (1989).

Cournoyer, et al. *Annu. Rev. Immunol.*, Gene Therapy of the Immune System, vol. 11, pp. 297–329 (1993).

Dingwall et al., *Proc. Natl. Acad. Sci USA*, Human immunodeficiency virus 1 tat protein binds trans–activation–responsive region (TAR) RNA in vitro, vol. 86, pp. 6925–6929 (1989).

Feinberg, et al., *Aids Research and Human Retroviruses*, Intracellular Immunization: Trans–Dominant Mutants of HIV Gene Products as Tools for the Study and . . . , vol. 8, No. 6, pp. 1013–1022 (1992).

Johnston, et al., *Science*, Present Status and Future Prospects for HIV therapies, vol. 260, pp.1286–1293 (1993).

Kessel, et al., *Molecular and Cellular Biology*, Nucleotide Sequence Analysis and Enhancer Function of Long Terminal Repeats Associated with an Endogenous African Green Monkey Retroviral DNA, vol. 5, pp. 1335–1342 (1985).

Rosen, C.A., *Trends in Genetics*, Regulation of HIV gene expression by RNA–protein interactions, vol. 7, pp. 9–14 (1991).

Sarver, et al., *Science*, Ribozymes as Potential Anti–HIV–1 Therapeutic Agents, vol. 247, pp. 1222–1225 (1990).

Sharp, et al., *Cell*, HIV TAB: An RNA Enhancer? vol. 59, pp. 229–230 Oct., 1989.

Siekevitz, et al., *Science*, Activation of the HIV–1 LTR by T Cell Mitogens and the Trans–Activator Protein of HTLV–1, vol. 238, pp. 1575–1578 (1987).

Trono, et al., *Cell*, HIV–1 Gag Mutants Can Dominantly Interfere with the Replication of the Wild–Type Virus, vol. 59, pp. 113–120 (1989).

Mitsuya et al., Nature 325:773–778 (1987).*

Chang et al., *J. Cell. Biochem.*, Suppl. 16E, p. 76, abstract Q509 (1992).

J. Lisziewicz, et al. (1993) "Inhibition of Human Immunodeficiency Virus Type 1 Replication by Regulated Expression of a Polymeric TAT Activation Respone RNA Decoy as a Strategy for Gene Therapy in AIDS", *Proc. Natl. Acad. Sci. USA*, 90:8000–8004.

"Report and Recommendations of the Panel to Assess the NIH Investment in Research on Gene Therapy," Orkin and Motulsky, Co–chairs, Dec. 7, 1995.*

H.K. Chang, et al.; Gene Therapy, vol. 1, No. 3, May 1994; pp. 208–216; "Block of HIV–1 Infection by a Combination of Antisense tat RNA and DNA decoys: a strategy for control of HIV–1".

Gilboa et al., Trends in Genetics 10(4):139–144 (1994).*

* cited by examiner

*Primary Examiner*—Remy Yucel
(74) *Attorney, Agent, or Firm*—Knobbe, Martens, Olson & Bear, LLP

(57) ABSTRACT

The present invention relates to viral inhibition, particularly HIV inhibition, by DNA sequences including multiple target response elements. The DNA construct of the present invention comprises a vector and a promoter operably linked to at least one target response element and, optionally, to other viral inhibitory elements, so that the elements are transcribed in tandem. The DNA construct can be used in the treatment of viral infections, HIV in particular, by obtaining cells from an HIV-infected patient, transforming the cells with the construct and administering the transformed cells to the patient. The protective gene product will only be expressed if the cell becomes infected and a viral protein is made.

11 Claims, 21 Drawing Sheets

ANNEALED OLIGOS:

+1                                                                                                                +63
5'- GGGTCTCTCTGGTTAGACCAGATCTGAGCCTGGGAGCTCTCTGGCTAACTAGGGAACCCACTGTTT
3'- CCCAGAGAGACCAATCTGGTCTAGACTCGGACCCTCGAGAGACCGATTGATCCCTTGGGTGACAAA

T4-LIGASE
Dra I & Sma I

DNA  5'- GGG.....TTTGGG.....TTTGGG.....TTTGGG.....TTTG →
     3'- CCC.....AAACCC.....AAACCC.....AAACCC.....AAA →

RNA          ACUGUUU      ACUGUUU      ACUGUUU      ACUGUUU →
      +1 G—C          G—C          G—C          G—C
         G—C          G—C          G—C          G—C
         G—C          G—C          G—C          G—C
        U—A          U—A          U—A          U—A
       C U—A        C U—A        C U—A        C U—A
         C—G          C—G          C—G          C—G
         U G          U G          U G          U G
         C—G          C—G          C—G          C—G
         U—A          U—A          U—A          U—A
         G U          G U          G U          G U
         G—C          G—C          G—C          G—C
         U—A          U—A          U—A          U—A
         U—A          U—A          U—A          U—A
         A—U          A—U          A—U          A—U
        G—C          G—C          G—C          G—C
       A C—G        A C—G        A C—G        A C—G
         C—G          C—G          C—G          C—G
         A—U          A—U          A—U          A—U
         G—C          G—C          G—C          G—C
        A—U          A—U          A—U          A—U
         U            U            U            U
       C              C            C            C
        U G—C         U G—C        U G—C        U G—C
         A—U          A—U          A—U          A—U
         G—C          G—C          G—C          G—C
         C—G          C—G          C—G          C—G
         C   A        C   A        C   A        C   A
         U  GG G      U  GG G      U  GG G      U  GG G

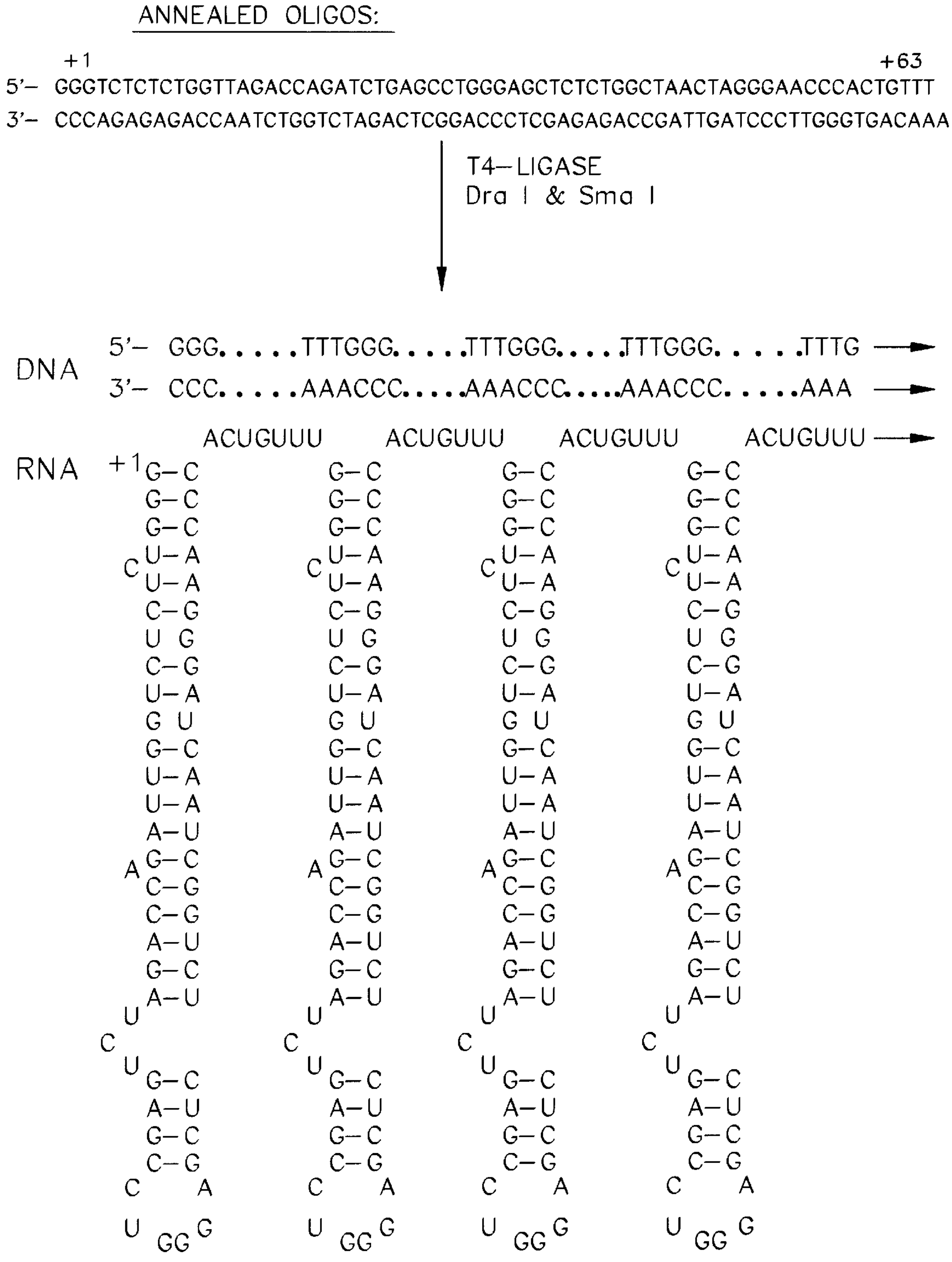

FIG. 2A

| LTR-CAT | + | + | + | + | + |
|---|---|---|---|---|---|
| LTR-TAT | + | + | + | + | + |
| LTR-5TAR | — | 10x | 25x | 40x | 50x |
| LTR-OTAR | 50x | 40x | 25x | 10x | — |

| LTR-CAT | + | + | + | + |
|---|---|---|---|---|
| LTR-TAT | + | + | + | + |
| LTR-5TAR | — | 15x | 35x | 50x |
| LTR-OTAR | 50x | 35x | 15x | — |

INHIBITION OF VIRAL REPLICATION: RNA LEVEL

A. LTR IS RESPONSIBLE FOR THE PHYSIOLOGICAL REGULATION

B. MULTIPLE TAR INHIBITS THE VIRAL GENE EXPRESSION

C. RIBOZYME (GAGHAM) INHIBTS GAG EXPRESSION

D. RRE TRANSPORTS THE TRANSCRIPT TO THE CYTOPLASM

THE CONSTRUCT WILL BE PLACED IN A RETROVIRAL VECTOR TO ENSURE HIGH EFFICINY GENE TRANSFER

INHIBITION OF HIV REPLIICATION: FUNCTIONAL INHIBITION STRATEGY

ADVANTAGES: THIS STRATEGY WORKS INDEPENDENTLY OF VIRAL MUTATIONS

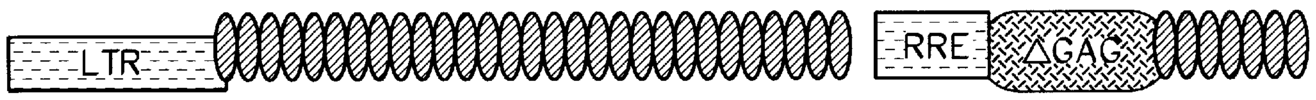

A. LTR IS RESPONSIBLE FOR THE PHYSIOLOGICAL REGULATION

B. MULTIPLE TAR INHIBITS THE VIRAL GENE EXPRESSION

C. RRE TRANSPORTS THE TRANSCRIPT TO THE CYTOPLASM

D. ΔGAG INHIBITS THE VIRAL RELEASE

THE CONSTRUCT WILL BE PLACED IN A RETROVIRAL VECTOR TO ENSURE HIGH EFFICINY GENE TRANSFER

FIG. 7

VECTOR WITH MULTIPLE TARGET RESPONSE ELEMENTS AFFECTING GENE EXPRESSION

This application is a continuation-in-part of prior application Ser. No. 08/069,476, filed Jun. 1, 1993 now abandoned, which is a continuation of prior application Ser. No. 07/596,299 filed Oct. 15, 1990 now abandoned, which is a continuation-in-part of prior application Ser. No. 07/467,407 filed Jan. 18, 1990 now abandoned, the entire contents of which are hereby incorporated by reference.

BACKGROUND OF THE INVENTION

The *Escherichia coli* LTR-7TAR, Bj, rec B-, has been deposited on Jan. 17, 1990 in the American Type Culture Collection (ATCC), 10801 University Blvd, Manassas, Va. 20110 under the accession number 68203.

1. Field of the Invention

The present invention relates to a method of effecting viral inhibition with DNA sequences encoding multiple target response elements, and to constructs suitable for use in same. In particular, the invention relates to a method of inhibiting replication of the Human Immunodeficiency Virus (HIV).

2. Background Information

The tat protein of HIV transactivates viral gene expression and is essential for production of viral products (Arya et al., *Science* 229:69–73 (1985); Sodroski, et al., *Science* 229:74–77 (1985); Dayton, et al., *Cell* 44:941–947 (1986); Fisher, et al., *Nature* 320:367–371 (1986)). The tat activation response element (TAR) has been localized within the region of the first 44 nucleotides downstream of the transcription initiation site (Chen and Okayama, *Mol. Cell. Biol.* 7:2745 (1987); Rosen, et al., *Cell* 41:813–823 (1985); Tong-Starksen, et al., *Proc. Natl. Acad. Sci., USA* 84:6845–6849 (1987); Haruber, et al., *J. Virol.* 62:673–679 (1988)). This region, present in all HIV-1 transcripts, forms an unusually stable stem loop structure (Okamoto and Wong-Staal, *Cell* 47:29–35 (1986)), and several lines of evidence suggest that the transcriptional effect of tat is mediated through interaction with the TAR region of viral RNA (Sharp, et al. *Cell* 59:229–230 (1989); Viscidi, et al., *Science* 246:1606–1608 (1989); Berkhout, et al., *Cell* 59:273–282 (1989); Garcia, et al., *EMBO J.* 8:765–778 (1989); Feng and Holland, *Nature* 334:165–167 (1988); Southgate, et al., *Nature* 345:640–642 (1990)).

While tat binding to TAR RNA sequences has been demonstrated (Rappaport, et al., Cold Spring Harbor, N.Y. (1989b); Dingwall, et al., *Proc. Natl. Acad. Sci. USA* 86:6925–6929 (1989)), the sequence requirements for tat binding are not sufficient to explain the sequence and structural requirements needed for transactivation. Cellular factors also appear to play a role in tat mediated transactivation which may confer additional specificity (Marciniak, et al., *Proc. Natl. Acad. Sci.* 87:3624–3628 (1990)). Tat appears to function poorly in nonprimate cells and studies using interspecific hybrids suggest that transactivation potential is correlated with the presence of human chromosome 12 (Hart, et al., *Science* 246:488–491). Several cellular TAR RNA as well as TAR DNA binding proteins have been identified (Gaynor, R. B. *EMBO J.* 8:765–778 (1989); Gatignol, et al., *Proc. Natl. Acad. Sci. USA* 86:7828–7832 (1989); Wu, et al., *EMBO J.* 7:2117–2129 (1988); Jones, et al., *Science* 232:755–758 (1986); Garcia, et al., *EMBO J.* 8:765–778 (1989); Marciniak, et al., *Proc. Natl. Acad. Sci.* 87:3624–3628 (1990)), although the role of these proteins in tat mediated transactivation is unclear.

In vitro, tat protein can be released and taken up by cells (Frankel and Pabo, *Cell* 55:1189–1193 (1988)), and has biological effects on the regulation of cellular proliferation in addition to its role in HIV promoter activation. Recent studies indicate that tat inhibits antigen-induced lymphocyte proliferation, (Viscidi, et al., *Science* 246:1606–1608 (1989)), has growth promoting activity on cells derived from Kaposi Sarcoma lesions of AIDS patients (Ensoli, et al., *Nature* 340:84–86 (1990)) and stimulates the production of inflammatory cytokines (Buonaguro et al., (1992) *J. Virol.,* 66:7159–7167). In contrast, tat does not cause significant reduction of lymphocyte proliferation in response to mitogens. Since the tat protein is critical to HIV replication and the onset of AIDS, interference with tat function will be therapeutically significant.

Transdominant mutations of HIV proteins have been reported (Malim, et al., *Cell* 58:205–214 (1989); Torno, et al., *Cell* 59:113–120 (1989); Marciniak, et al., *Proc. Natl. Acad. Sci.* 87:3624–3628 (1990). These proteins, produced constitutively from a strong promoter, can antagonize the growth of HIV-1 and, therefore, can be used to create cell lines "immunized" to viral infection.

Since TAR RNA appears to interact with tat protein directly (Southgate, et al., *Nature* 345:640–624 (1990)) or through the combined activities of cellular factor(s) (Marciniak, et al., *Proc. Natl. Acad. Sci. USA* 87:3624–3628 (1990), we hypothesized that TAR RNA, produced in large amounts, might serve as a competitive inhibitor of tat function.

SUMMARY OF THE INVENTION

One embodiment of the present invention is a DNA construct having a vector and a promoter operably linked to at least two DNA segments encoding HIV-1 tat activation response (TAR) elements so that the elements are transcribed in tandem. Preferably, the promoter is a primate lentivirus LTR. Most preferably, the LTR is the Human Immunodeficiency Virus-1 (HIV-1) LTR. Advantageously, the DNA construct between 5 and 50 TAR elements. In addition, the DNA construct the promoter in this embodiment can preferably be regulated by the HIV-1 tat protein. A preferred vector in this embodiment is pCD7. More preferably, the vector is a retroviral vector and the retroviral vector is either DC-antitat/30 or DC-antitat/23. Still more preferably, the vector has a DNA segment encoding tat antisense RNA. Most preferably, the tat antisense RNA and the TAR sequences are on the same RNA molecule.

Another embodiment of the present invention is a method of treating lentivirus infection. This method has the following steps.

(i) obtaining cells from a lentivirus-infected patient;

(ii) introducing the lentivirus-inhibiting construct according to Claim 1 into the cells;

(iii) expanding the cells in culture; and (iv) reintroducing cells resulting from step (iii) to the patient under conditions such that the treatment is effected.

Advantageously, the lentivirus in this method is HIV-1. In addition, the cells can be bone marrow cells or blood cells. More preferably, the blood cells are $CD4^+$ T-cells. In an even more advantageous embodiment, the number of the $CD4^+$ T-cells increases as a result of the introduction of the construct. In this method, the expanding step might involve treatment with a mitogen, with a preferable mitogen being phytohemagglutinin. During this method, the cells can be cultured in the presence of a cytokine, such as interleukin-2, after treatment with the mitogen. Also, during this method, the construct introduced in step (ii) can be a DNA construct having a vector with a promoter operably linked to at least two HIV-1 TAR elements and to a sequence encoding a molecule that inhibits lentivirus replication, wherein the TAR elements and the sequence are transcribed together in the same transcript.

Yet another embodiment of the present invention is a method for protecting against lentivirus infection by the steps of:

(i) obtaining cells from an asymptomatic individual;

(ii) introducing the lentivirus-inhibiting construct according to Claim 1 into the cells;

(iii) expanding the cells; and (iv) reintroducing cells resulting from step (iii) to the individual under conditions such that the treatment is effected.

Advantageously, the lentivirus in this method can be HIV-1.

Still another embodiment of the present invention is a method of inhibiting lentivirus replication by introducing into lentivirus-infected cells the DNA construct discussed above under conditions such that inhibition is effected. Most preferably, the lentivirus is HIV.

Yet a further embodiment of the present invention is a method of inhibiting lentivirus replication by introducing into a lentivirus-infected cell the DNA construct discussed above wherein a lentivirus protein product regulates transcription of the lentivirus LTR so that the inhibition is effected. The lentivirus in this case is advantageously HIV.

A further embodiment of the present invention is a DNA construct having a vector with a promoter operably linked to at least two HIV-1 TAR elements and to a sequence encoding a molecule that inhibits lentivirus replication, wherein the TAR elements and the sequence are transcribed together in the same transcript. The lentivirus in this embodiment can preferably be HIV-1. Preferably, the molecule can be a RNA molecule, more preferably, the molecule is a ribozyme. Most preferably, the ribozyme is specific for HIV-1 RNA. Alternatively, the molecule can be an antisense RNA molecule, preferably a tat antisense RNA molecule. In yet another alternative, the molecule can be a protein, and the protein can be a transdominant negative mutant viral protein. In addition, the mutant viral protein can be a gag mutant protein.

A still further embodiment of the present invention is a DNA expression cassette encoding a plurality of TAR elements and antisense tat DNA, and operably linked to a lentivirus LTR promoter. The lentivirus LTR can advantageously be HIV-1 LTR and the expression cassette can be inserted into a retroviral vector. Alternatively, the vector can contain the murine moloney leukemia virus LTR.

In addition, the present invention includes an amphotropic packaging cell line having a cell containing the retroviral construct discussed above wherein the cell is capable of producing retroviral particles having the retroviral construct within their genome. Preferably, the cell line is PA317.

Yet another embodiment of the present invention is an inducible anti-HIV-1 DNA construct having an anti-HIV-1 gene operably linked to an HIV-1 LTR, wherein the HIV-1 LTR is activated only in the presence of HIV-1. Advantageously, the anti-HIV-1 gene is selected from the group consisting of: poly TAR elements, tat antisense RNA, anti-gag ribozyme and transdominant negative mutant gag protein.

According to this model, tat expressed from the viral LTR activates the LTR driven transcription of the multiple TAR elements. Multiple TAR RNA competes for tat binding. Therefore, viral gene expression and tat expression decrease until an equilibrium is reached, which is dependent on the number of TAR elements in the construct.

FIG. 2A shows the construction of the multiple TAR elements and the predicted secondary structure of the transcript.

The figure shows the annealed oligonucleotide containing the entire wild type TAR element with the half palindromic sequence of Dral and Smal. Arrows represent the direction of transcription. The predicted secondary structure of the multiple TAR RNA elements is also indicated.

Figure 2B:
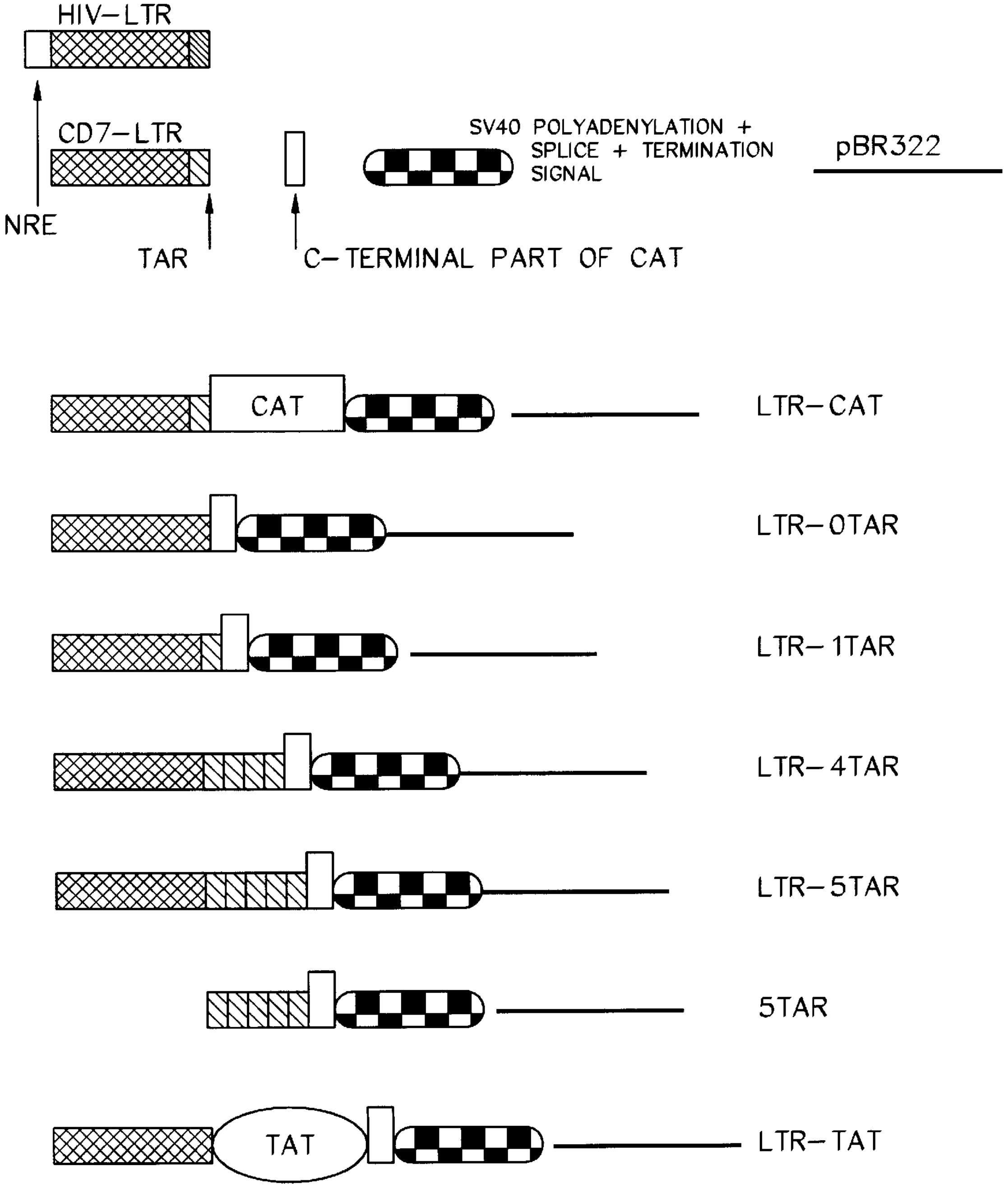

FIG. 2B shows the general structure of the inhibitory plasmids used in the transfection assays.

Plasmids used for this experiments contain the CD7-LTR, which is derived from the wild type HIV-1-LTR, by deletion of the negative regulatory element (NRE). All constructs contain the C-terminal part of the bacterial chloramphenicol acetyltransferase (CAT) gene (downstream from the NcoI site) and SV40 splice and polyadenylation signals.

Figure 3A:
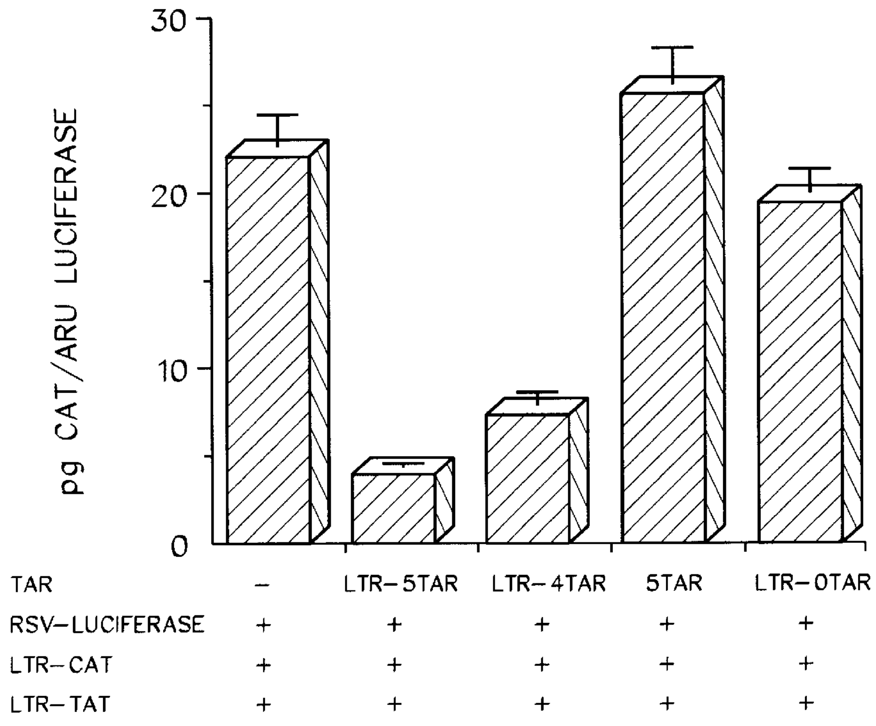

FIGS. 3A, B and D are graphs illustrating the poly TAR-induced inhibition of tat-mediated CAT gene expression. COS cells were cotransfected with 4.4 $\mu$g of different poly-TAR containing plasmids, 1 $\mu$g RSV-luciferase, 2.2$\mu$g LTR-CAT and 0.48 $\mu$g LTR-tat (Panel A) or 0.48 $\mu$g $PSV_L$-tat (Panel B) plasmids as indicated. In panel D, COS cells were cotransfected with 4.4 $\mu$g of the different poly-TAR containing expression plasmids, 1 $\mu$g luciferase, 2.2 $\mu$g HTLV-I-LTR-CAT, 0.48 $\mu$g HTLV-I-LTR-TAX and 0.48 $\mu$g LTR-tat as indicated. + and – represent the presence and absence of the particular plasmids in the cotransfection assay. Cell lysates were analyzed for CAT expression and luciferase activity 48 hours after transfection.

Figure 3B:
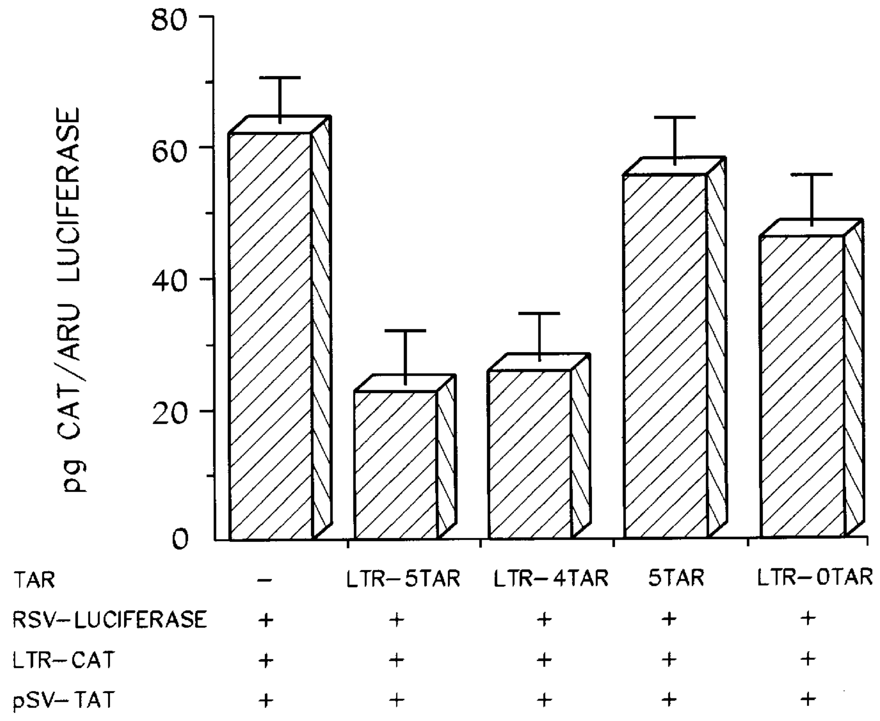
Figure 3C:
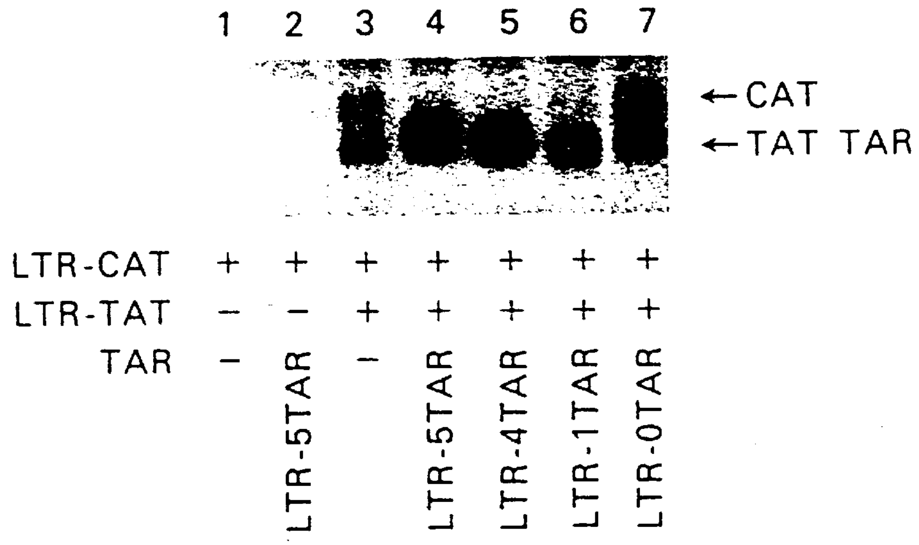

FIG. 3C is a Northern blot of RNA isolated from transfected cells and hybridized to a probe containing a fragment of the CAT gene. Total RNA was prepared from COS cells transfected with different plasmids indicated in the figure. + and – represent the presence and absence of the particular plasmids in the cotransfection assay. 10 $\mu$g RNA was analyzed by Northern blot hybridization. As shown in FIG. 2, the construct used for cotransfections contains a short C-terminal part of the CAT gene. A $^{32}$P-labelled nick-translated CAT fragment was used as a probe.

Figure 4A:
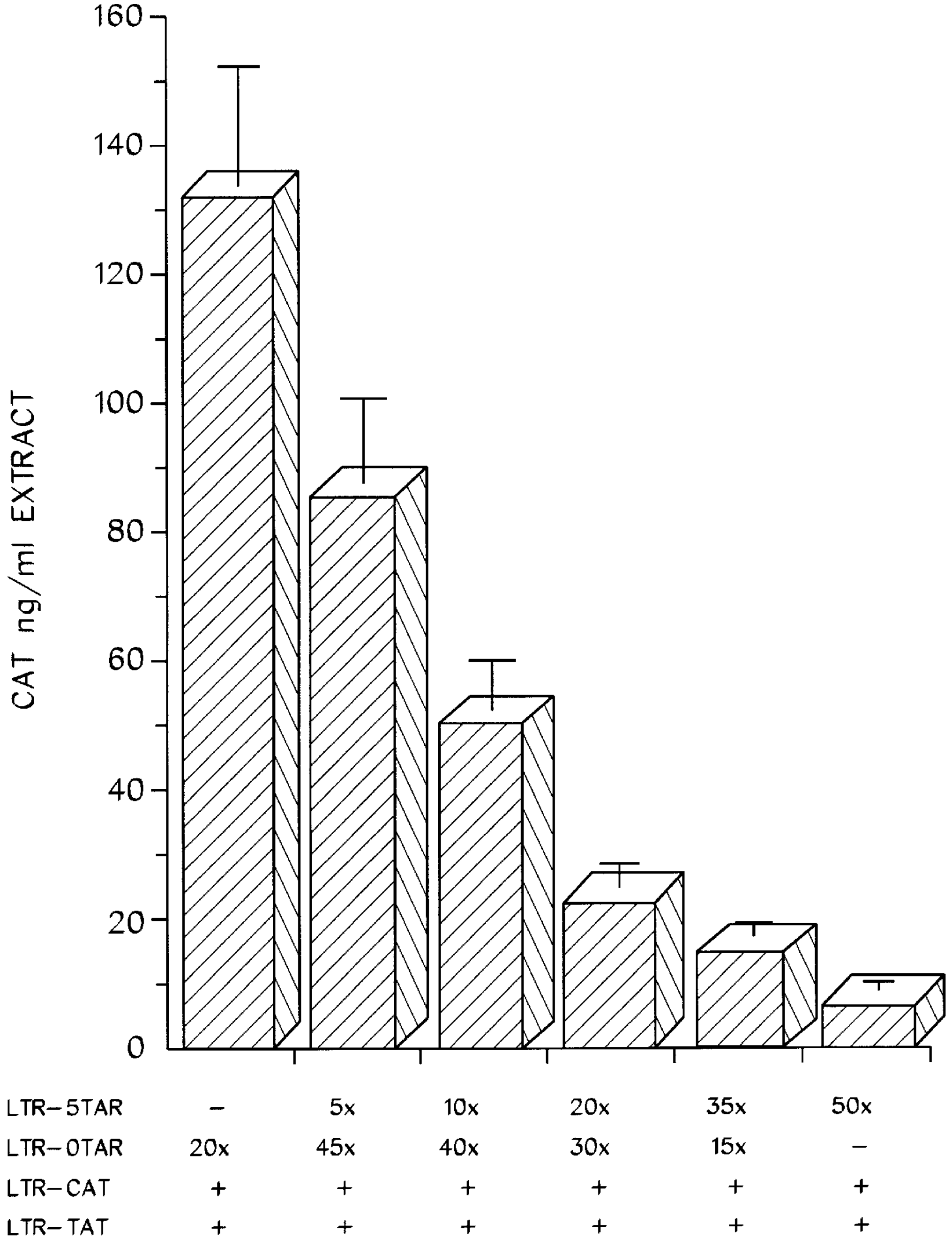

FIG. 4A is a graph illustrating the TAR RNA dose-dependent inhibition of tat-mediated transactivation. COS cells were cotransfected with 2.2 $\mu$g LTR-CAT, 0.48 $\mu$g LTR-tat and increasing amounts of LTR-5TAR. Decreasing amounts of LTR-OTAR (x indicates 0.22 $\mu$g) were used to keep the promoter concentration constant. + and – represent the presence and absence of each particular plasmid in the cotransfection assay. Cell lysates were analyzed for CAT expression 48 hrs after transfection.

Figure 4B:
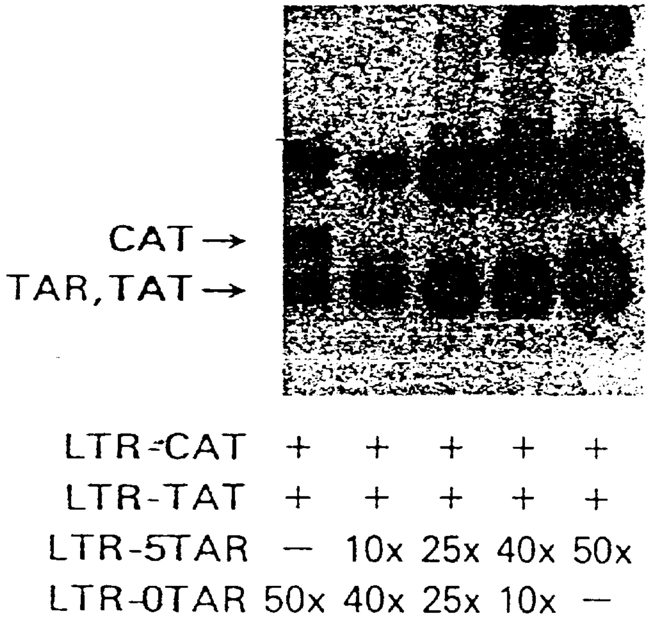

FIGS. 4B and C illustrate Northern blots of total RNA prepared from COS cells transfected with different plasmids. 10 $\mu$g RNA was analyzed by Northern blot hybridization using a nick translated, $^{32}$P-labelled CAT DNA fragment (Panel B). The CAT probe anneals to all constructs illustrated in FIG. 1. A $^{32}$P-labelled tat DNA probe was used to determine the amount of tat mRNA expressed under different conditions (Panel C).

Figure 5:
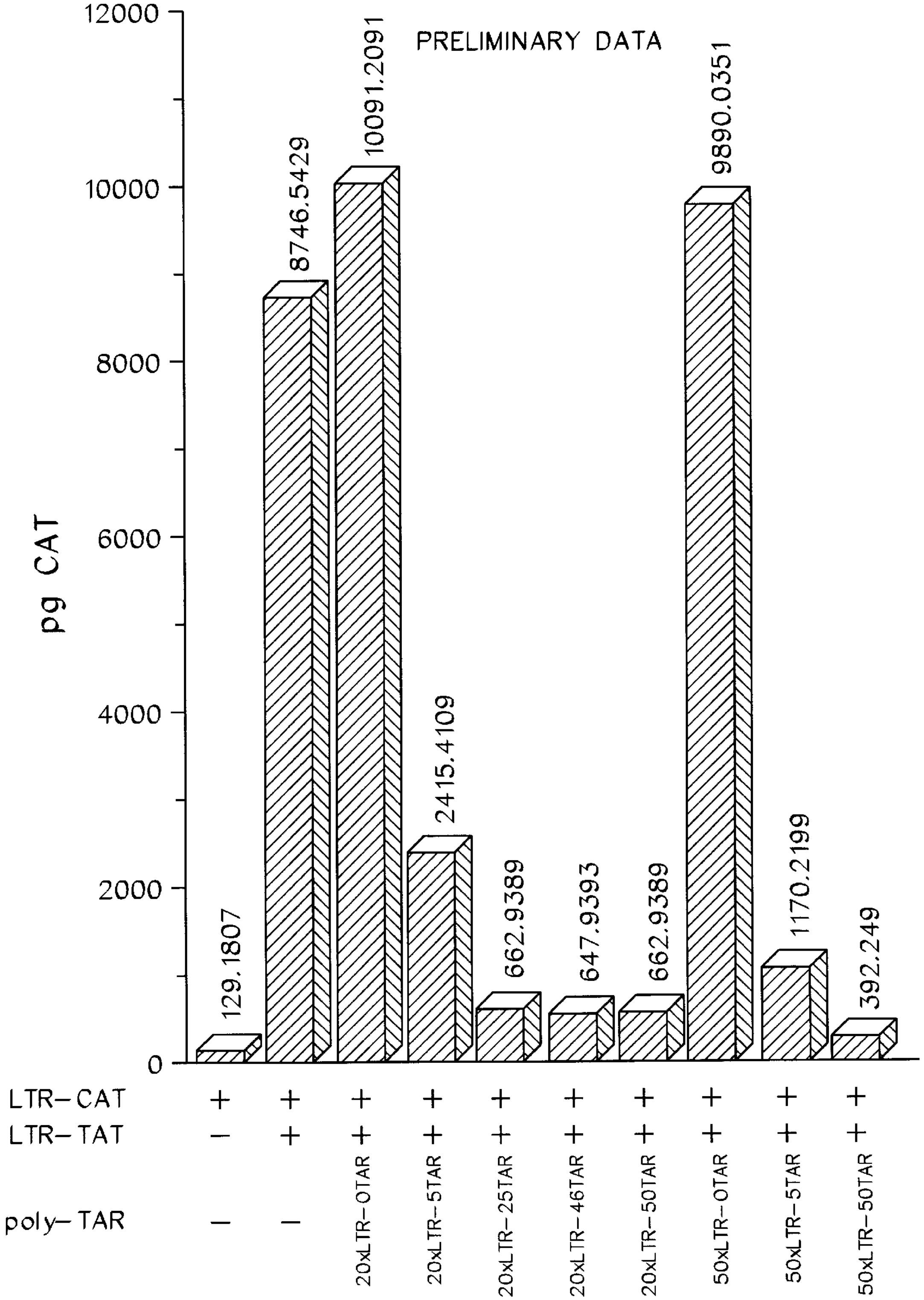

FIG. 5 is a graph illustrating the dependence of inhibition of transactivation on the amount of TAR RNA transcripts. The inhibition produced by constructs comprising 0 TAR to 50 TAR elements is compared. The poly TAR constructs used are shown on the x-axis and the level of CAT expression (pg) is shown on the y-axis.

Figure 6:
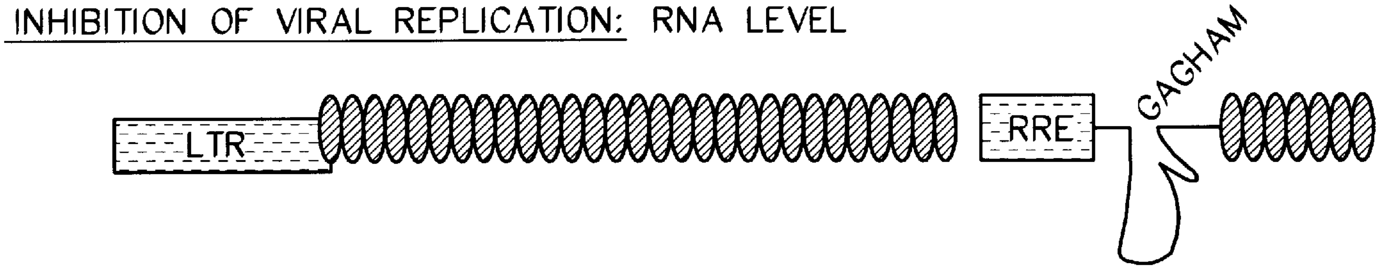

FIG. 6 is a schematic diagram of the ribozyme-poly-TAR construct used for inhibition of viral replication.

FIG. 7 shows an example of a ΔGAG-poly-TAR construct for inhibition of HIV replication.

Figure 8A:
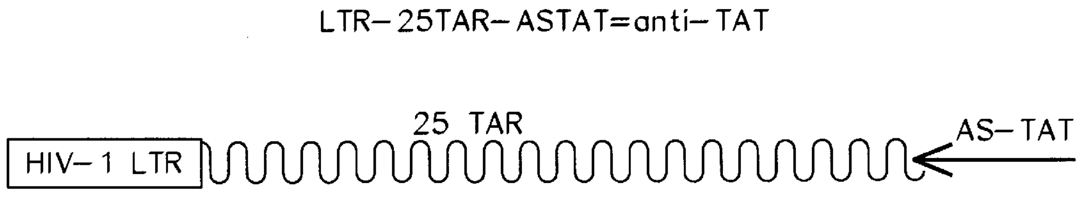

FIG. 8A is a schematic diagram of the antitat construct containing the 25 TAR elements and the Tat antisense gene (AS-TAT).

Figure 8B:
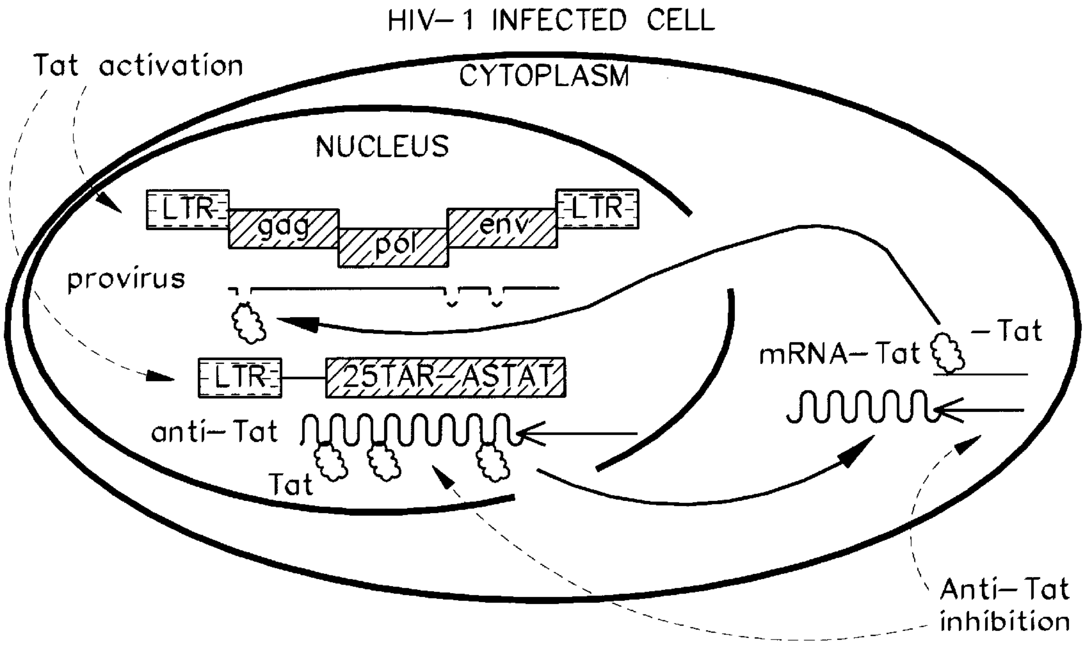

FIG. 8B is a schematic diagram illustrating the tat activation and inhibition pathways in an HIV-infected cell.

Figure 8C:
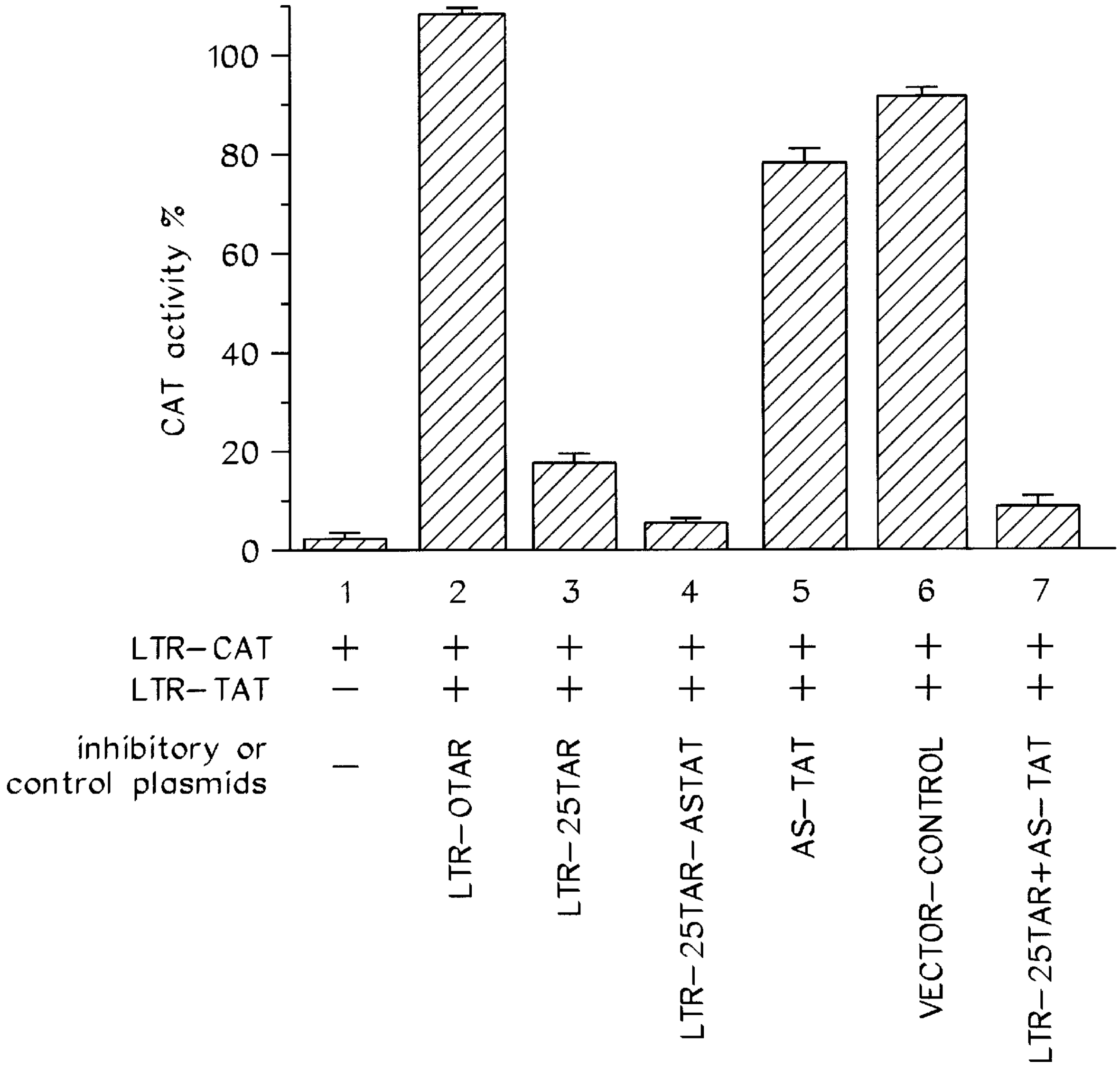

FIG. 8C shows inhibition of CAT expression after transduction of COS-1 cells with various DNA constructs.

Figure 9A:
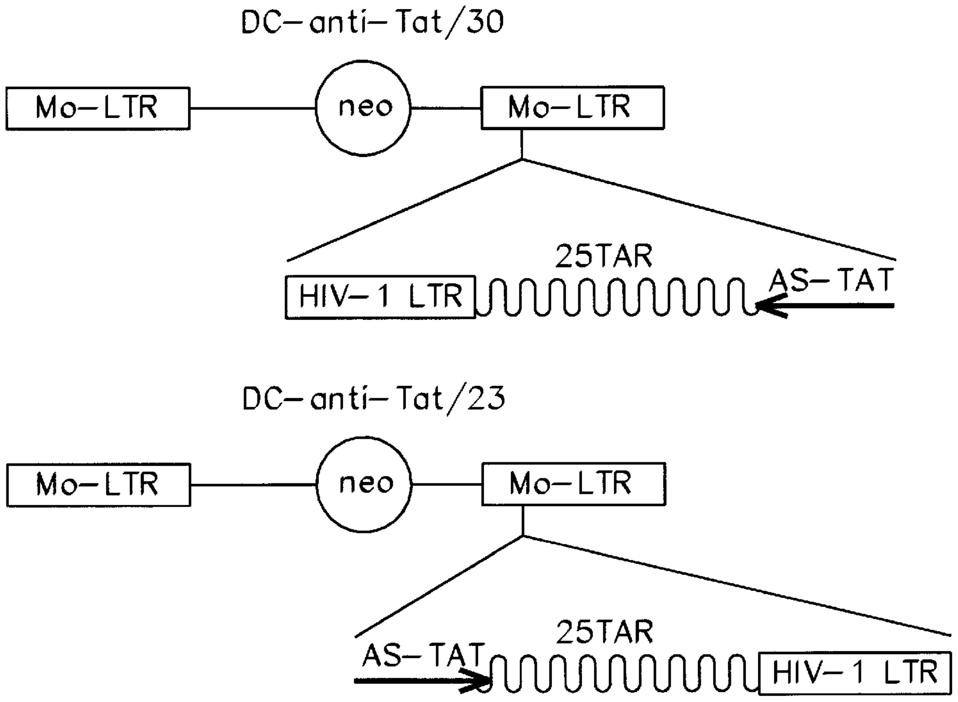

FIG. 9A is a schematic diagram of the antitat-containing retroviral vectors used to transduce immortalized and primary lymphocytes. The AS-TAT gene was inserted into the Murine Moloney Leukemia Virus long terminal repeat (Mo-LTR) in either the forward (DC-antitat/30) or reverse (DC-antitat/23) orientation. Neo=neomycin resistance.

Figure 9B:
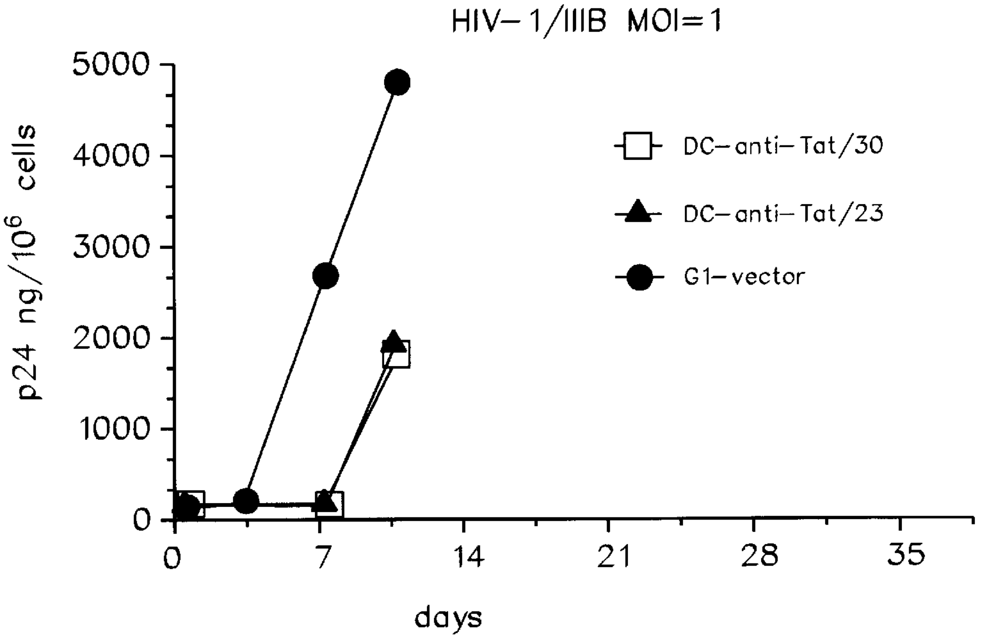
Figure 9C:
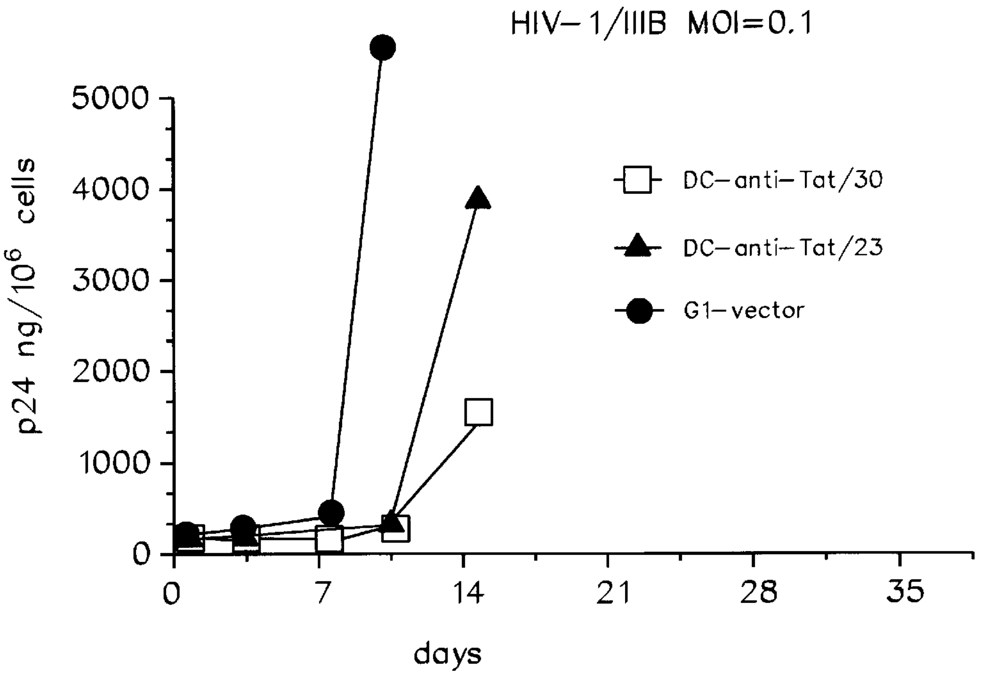
Figure 9D:
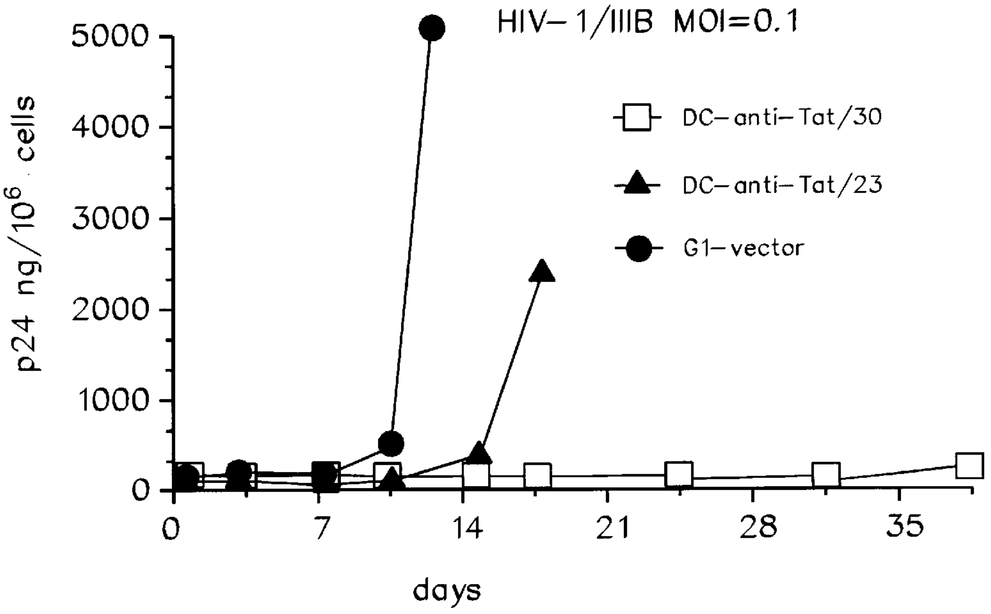

FIGS. 9B–D show the inhibition of HIV-1/HTLV-IIIB replication as measured by p24 antigen levels in Molt3 T-cells transduced with the antitat retroviral constructs and infected with HIV-1/HTLV-IIIB at multiplicities of infection (MOI) of 1, 0.1, and 0.01, respectively. The number of days post-infection is shown on the x-axis and the amount of p24 detected (ng/$10^6$ cells), an indicator of HIV replication, is shown on the y-axis.

Figure 10A:
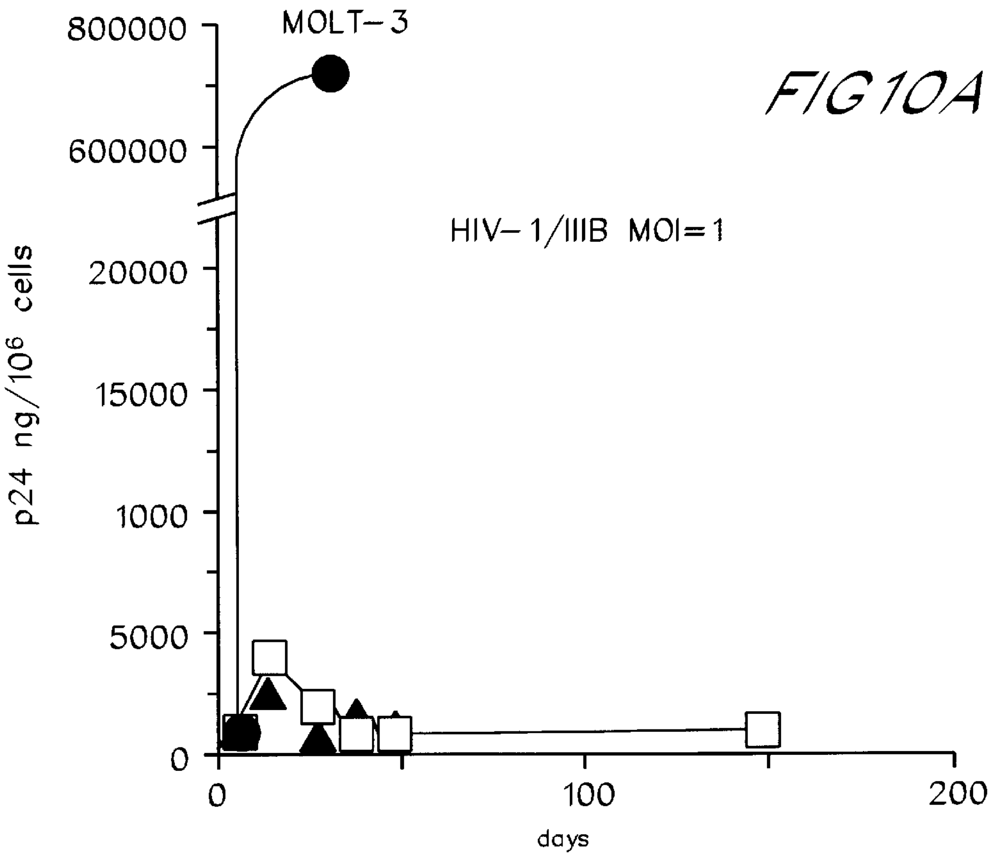

FIGS. 10A and B show the long term inhibition of HIV-1/HTLV-IIIB replication in antitat transduced Molt3 and CEM-ss cells, respectively. The number of days post-infection is shown on the x-axis and the amount of p24 detected is shown on the y-axis.

Figure 11A:
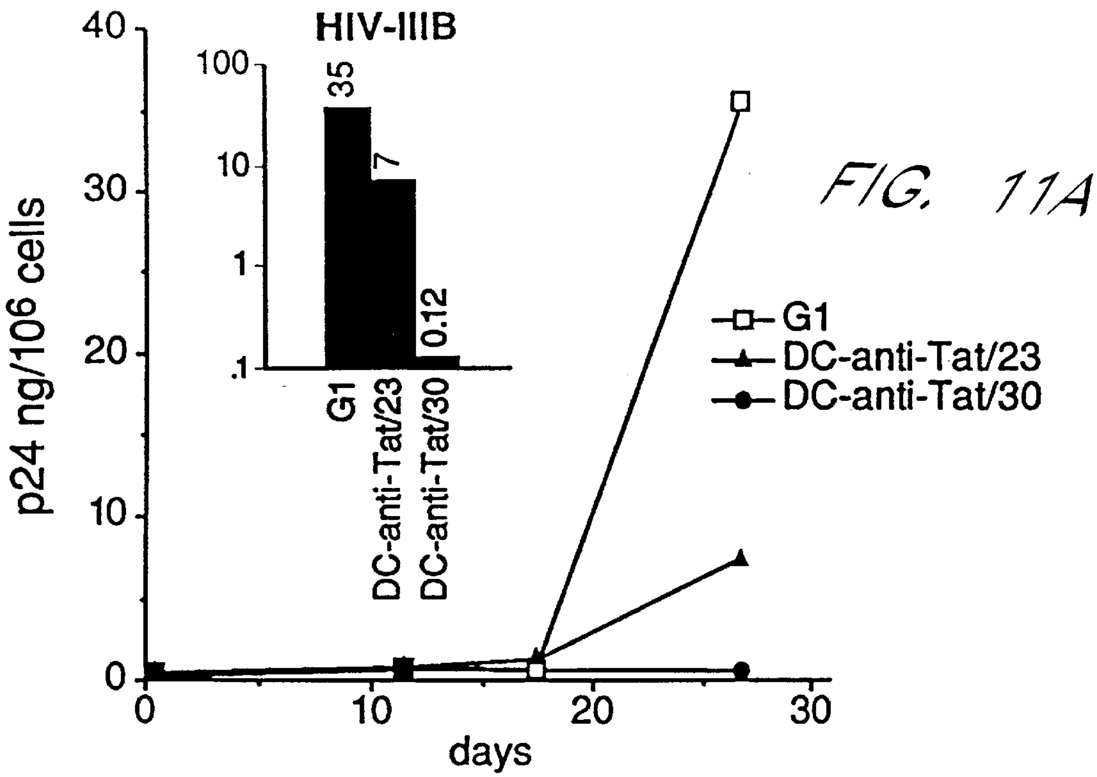

FIG. 11A shows the inhibition of HIV-1/HTLV-IIIB replication by the antitat retroviral vectors in normal human peripheral blood lymphocytes. The number of days post-infection is shown on the x-axis and the amount of p24 detected (ng/$10^6$ cells) is shown on the y-axis.

Figure 11C:
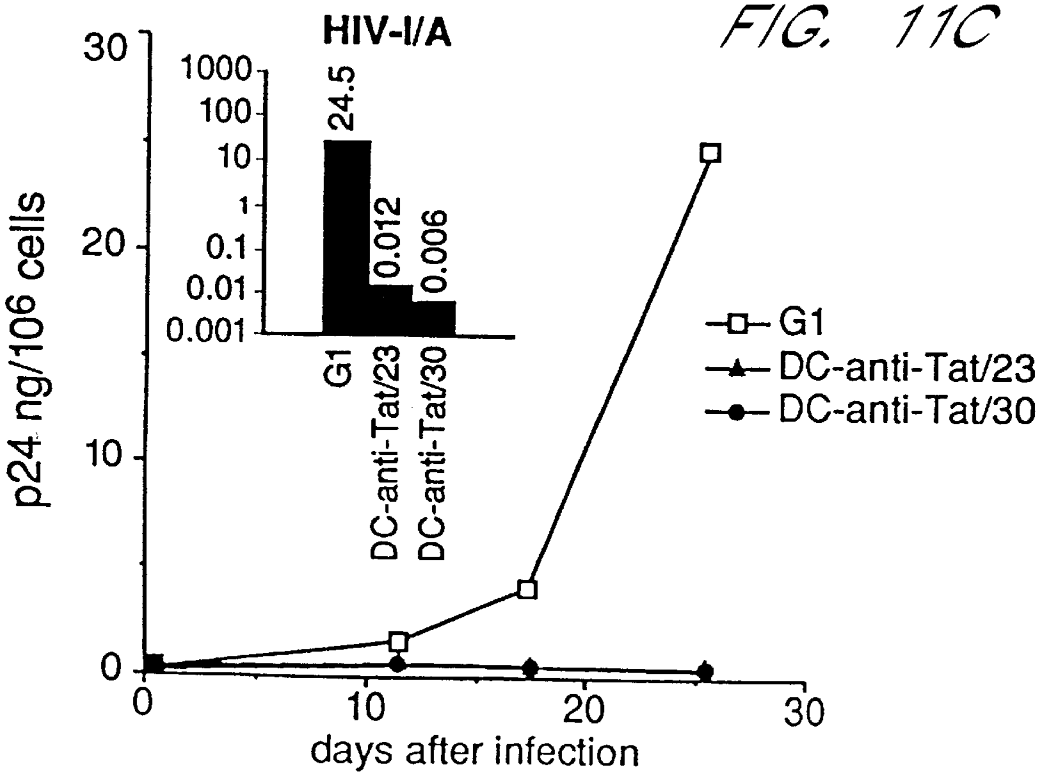
Figure 11B:
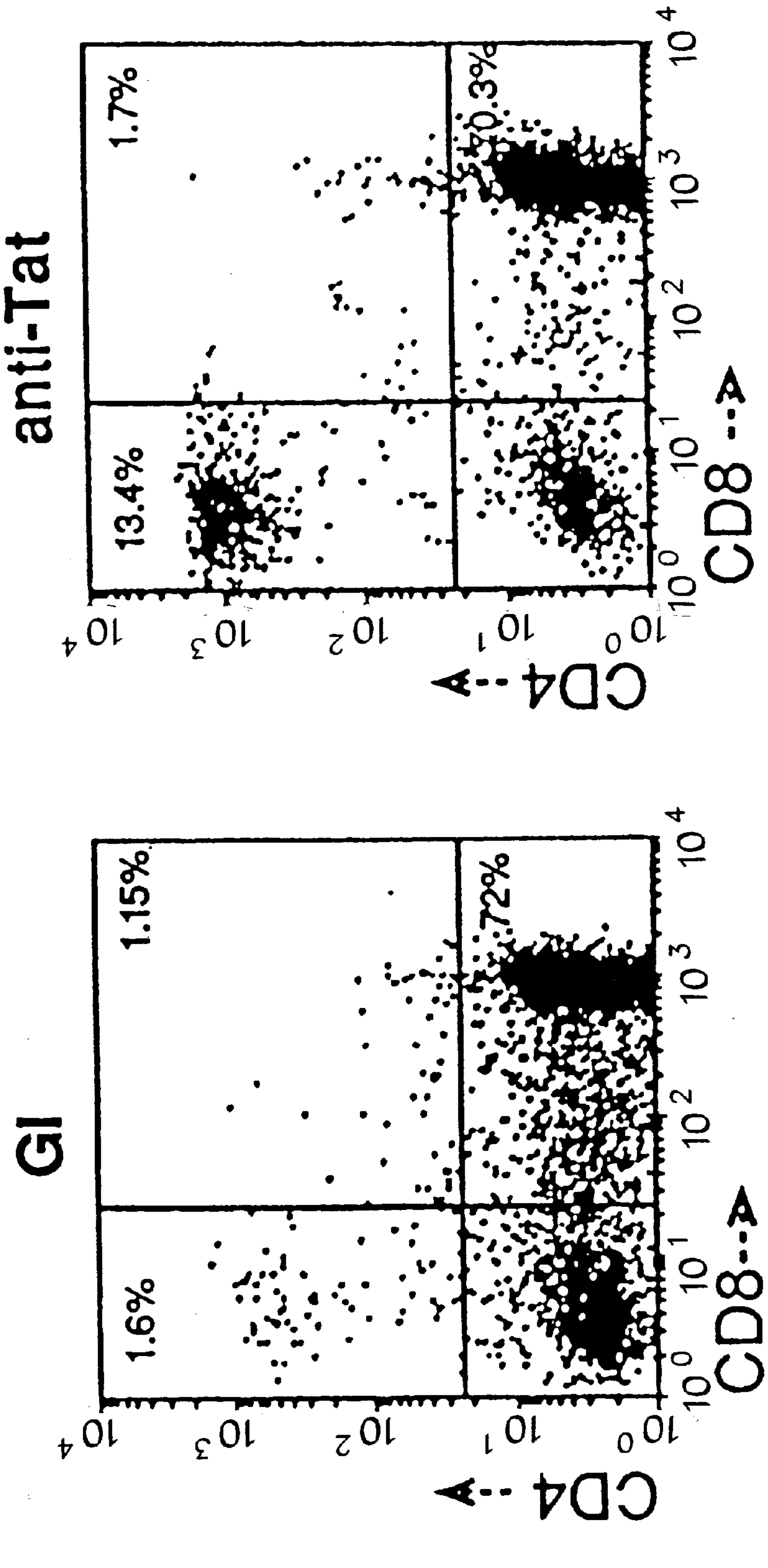

FIG. 11B shows the protection of T-cell cytopathic effect by the antitat gene. The figure shows a CD4/CD8 flow cytometry profile of normal human PBMCs transduced with an antitat retroviral vector or control vector and infected with HIV-1/HTLV-IIIB. An 8.5 fold increase in the number of $CD4^+$ cells was seen with the antitat retroviral vector compared to the Gl control vector.

FIG. 11C shows the complete inhibition of replication of the HIV3935 clinical isolate by the DC-antitat/23 and DC-antitat/30 retroviral vectors. The number of days post-infection is shown on the x-axis and the amount of p24 detected (ng/$10^6$ cells) is shown on the y-axis.

Figure 12A:
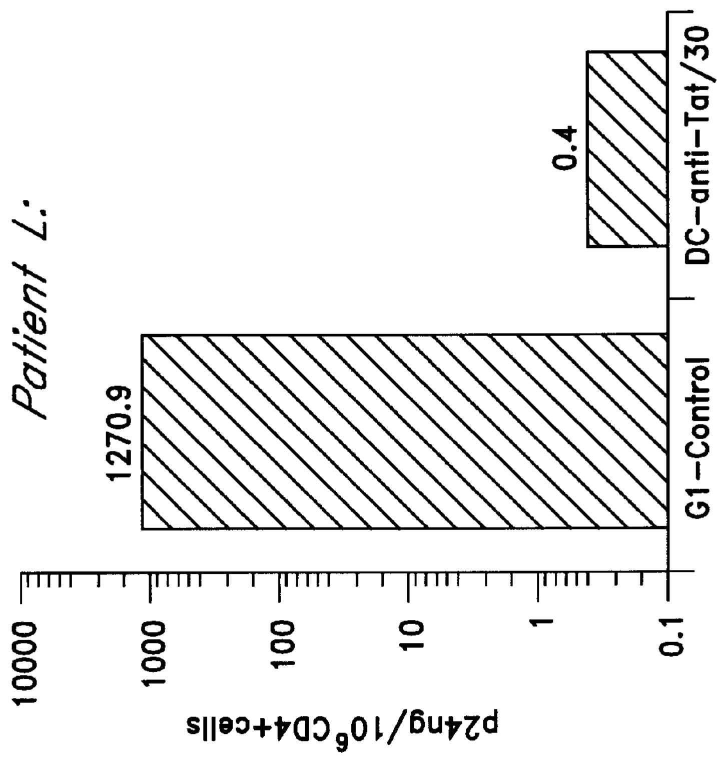

FIG. 12A shows the inhibition of viral replication by the DC-antitat/30 retroviral vector in PBMCs isolated from AIDS patient Li.

Figure 12B:
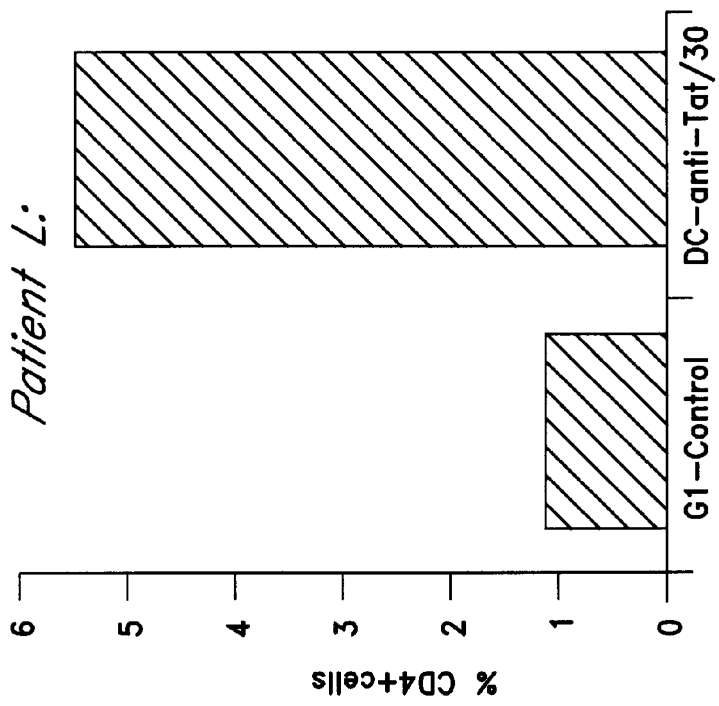

FIG. 12B shows the increase in the percentage of $CD4^+$ cells obtained after transduction of PBMCs from patient Li with the DC-antitat/30 retroviral vector.

Figure 13B:
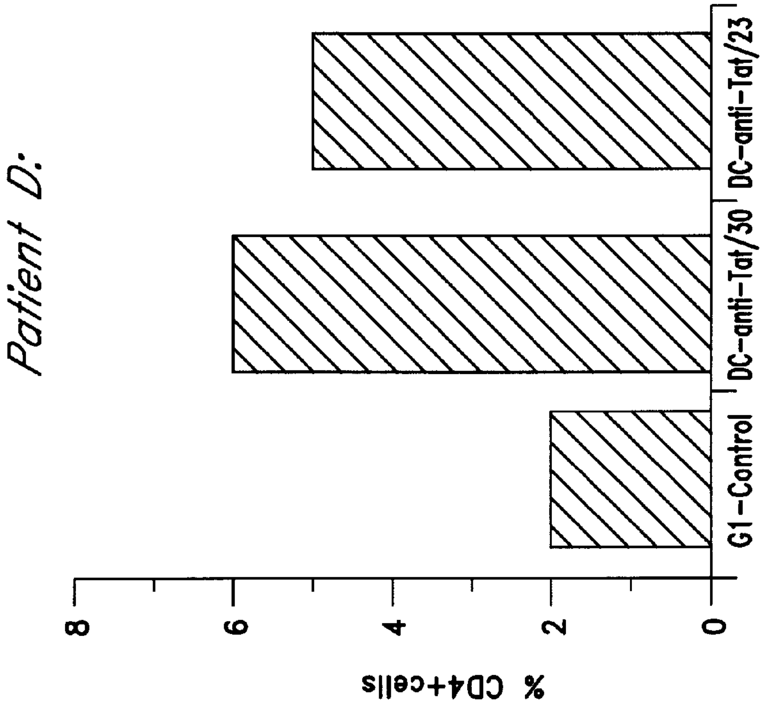
Figure 13A:
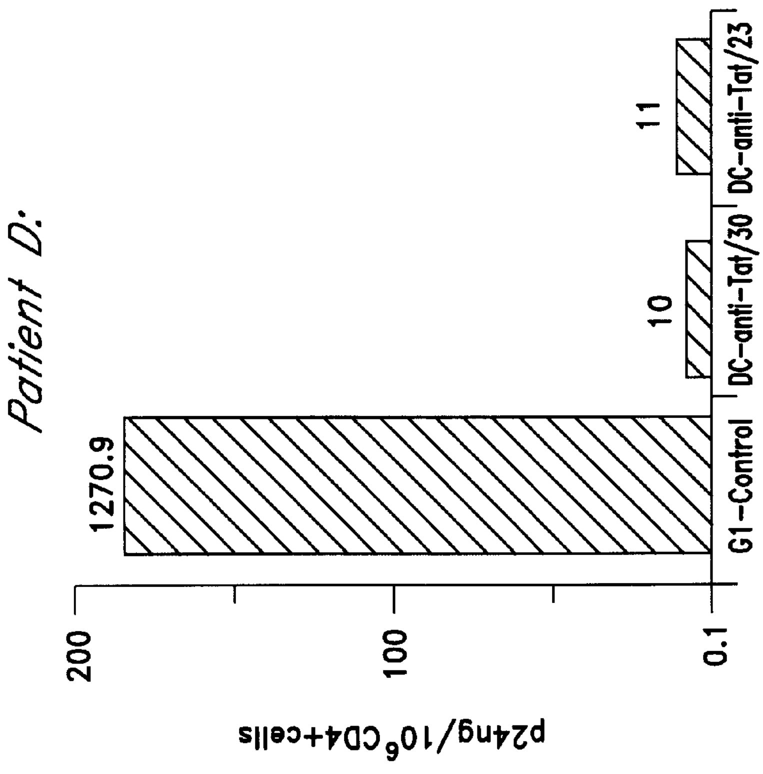

FIG. 13A illustrates the inhibition of viral replication by both the DC-antitat/30 and DC-antitat/23 retroviral vectors in PBMCs isolated from AIDS patient D.

FIG. 13B shows the increase in the percentage of $CD4^+$ cells obtained after transduction of PBMCs from patient D with both retroviral vectors containing the antitat gene.

Figure 14:
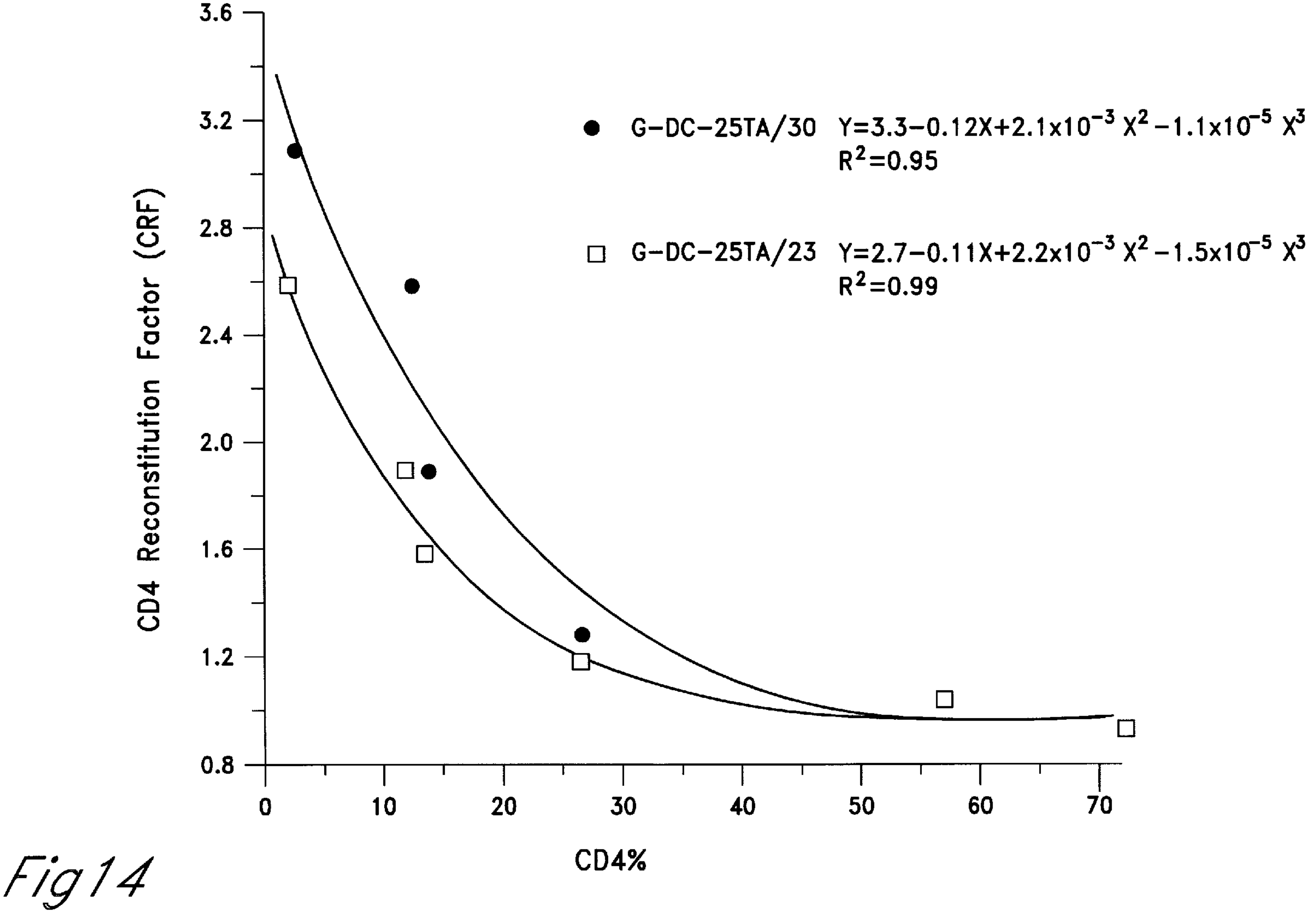

FIG. 14 is a graph illustrating the CD4 reconstitution factor (CRF) as a function of the percentage of $CD4^+$ T-cells (CD4%) om the unmodified control PBMCs. This plot can be mathematically approached by a polynomial curve. The constant of the polynomial shows the maximum effectiveness of an ex vivo gene therapy treatment. The CD4% is shown on the x-axis and the CRF is shown on the y-axis. G-DC-25TA/30 and G-DC-25TA/23 correspond to DC-antitat/30 and DC-antitat/23, respectively.

Figure 15:
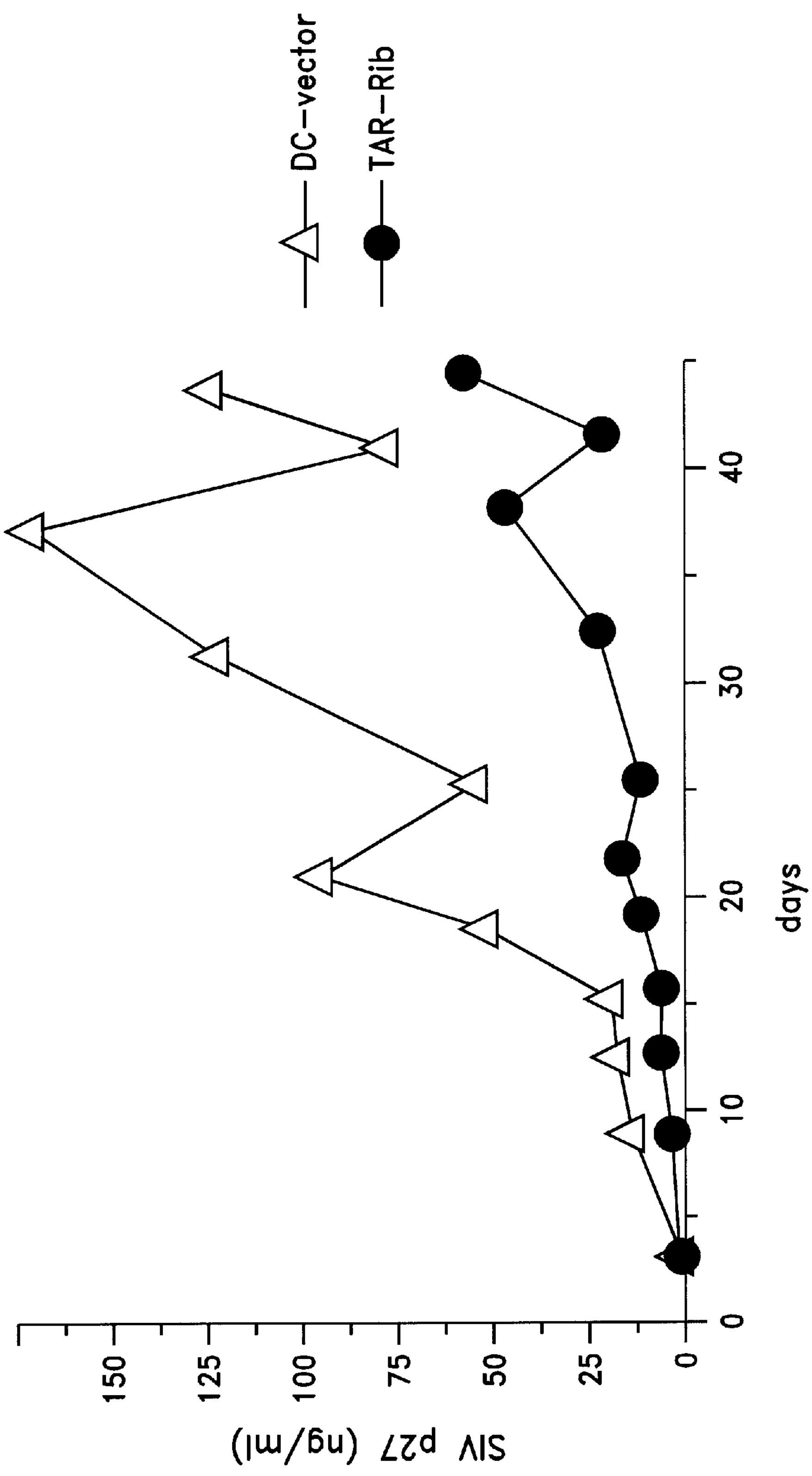

FIG. 15 is a graph illustrating the inhibition of SIV replication in Molt3 cells transduced with either a DC retroviral vector containing 50 TAR elements and the HIV-1 gag ribozyme or a control DC retroviral vector. The number of days post-infection is shown on the x-axis and the amount of p27 produced (ng/ml) is shown on the y-axis.

DETAILED DESCRIPTION OF THE INVENTION

The results presented in the Examples that follow indicate that overproduction of TAR RNA down regulates tat-mediated transactivation in a dose dependent manner. Biologically controlled expression of high levels of target RNA elements to sequester viral or cellular transactivators has general application in the development of a novel class of antiviral reagents.

The antitat construct of the present invention (containing DNA encoding 25 TAR elements and antisense tat DNA), when transfected into immortalized human T cells, exhibited anti-HIV-1 activity for five months, indicating its utility as a potent antiviral agent. The antitat construct also inhibited replication of both a "laboratory" strain of HIV-1 and a highly virulent primary clinical HIV-1 isolate in normal human T-cells transfected with the construct and subsequently infected with the virus. Importantly, the construct inhibited HIV-1 replication in T-cells isolated from AIDS patients with established HIV-1 infection. In fact, the antitat construct not only blocked HIV-1 replication, but also protected $CD4^+$ lymphocytes from the cytopathic effects of the virus and resulted in an expansion of the number of $CD4^+$ T-cells.

The constructs described herein containing the HIV-1 LTR promoter are advantageously expressed only in virus-infected cells since they can only be activated by the tat viral protein product. This is a significant advantage over prior art anti-HIV targeting methods since the accumulation of potentially toxic products in normal cells transfected with the construct will not occur due to the absence of the tat transactivator protein. In addition, the RNA products expressed by tat-mediated transactivation, namely ribozymes and RNA response elements, act to specifically inhibit a viral product by either binding to it and preventing its transactivation of essential viral genes or by specifically cleaving an essential viral mRNA. Since no protein products are being expressed from these constructs, the possibility of cell toxicity is greatly diminished. A particular advantage of using the HIV-1 LTR in stem cell therapy is that the activity of this promoter is not turned down during T-cell maturation.

These inducible transcripts having multiple adjacent sequences (poly TAR), exemplified herein, can be combined with coding sequences for trans-dominant mutant viral proteins, ribozymes or antisense RNA to provide a synergistic approach to intracellular immunization. Although TAR elements linked to the HIV-1 LTR are exemplified herein, the use of other RNA elements operably linked to this promoter or other viral promoters capable of being activated by viral proteins is also contemplated. For example, tandemly transcribed rev response elements (RREs) are expected to act as inhibitors of HIV-1 replication by binding the rev protein necessary for transport of the transcribed viral mRNA from the nucleus to the cytoplasm. This will result in the inability of the viral mRNAs to be translated by cytoplasmic ribosomes, thus inhibiting viral replication.

Figure 1:
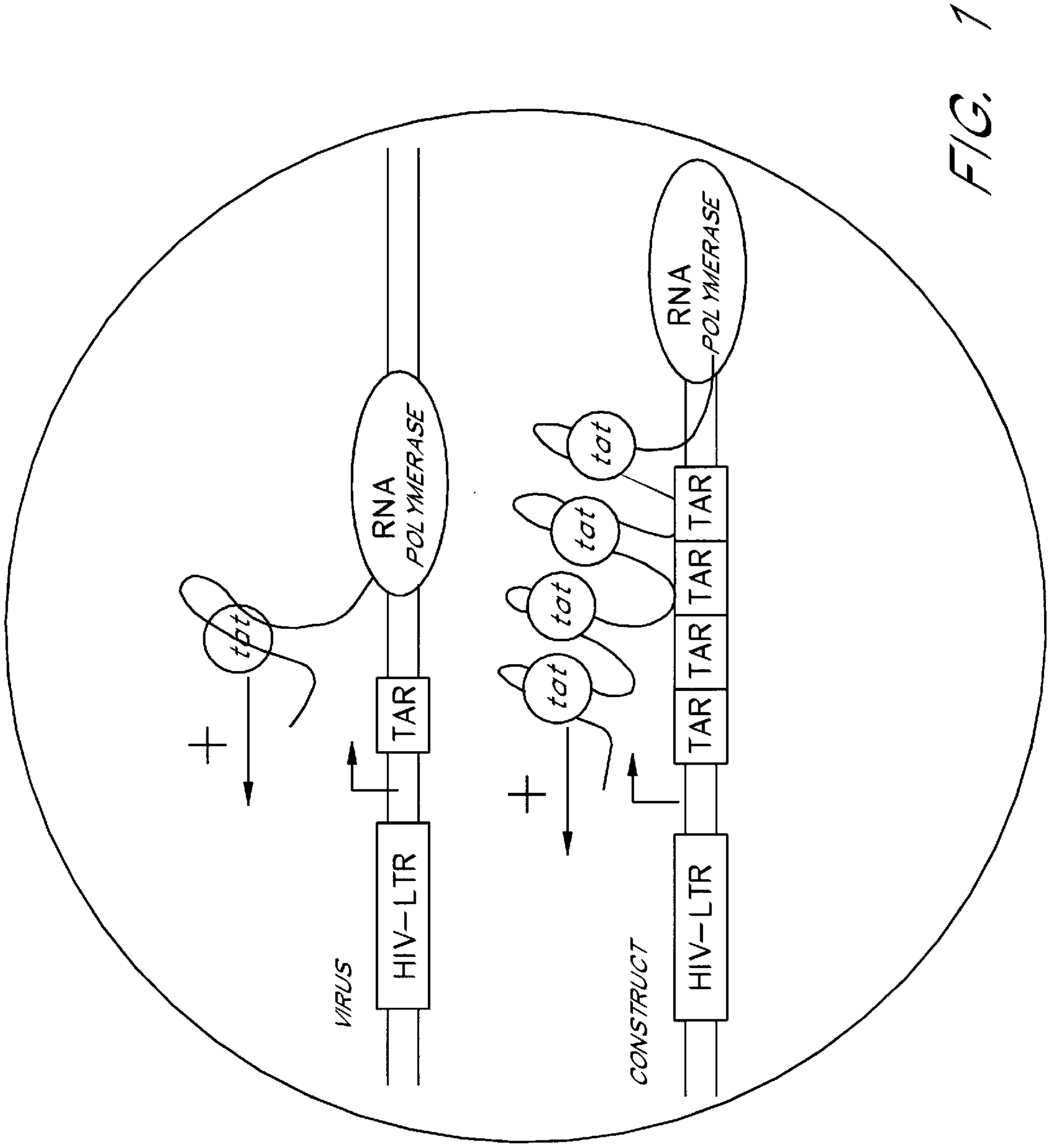
FIG. 1 shows the working hypothesis for intracellular inhibition of HIV gene expression using HIV-LTR-driven multiple TAR elements.

The specific aim of the studies leading to the present invention was to establish an inducible vector system which was activated by the action of tat protein and which could concomitantly inhibit tat activity. Thus, the present invention could be used as a method for inhibiting HIV replication. The approach involved inhibiting tat function by overproduction of TAR elements as shown in FIG. 1. Protected cells contain at least one copy of the construct of the present invention, and, after infection, one copy of the integrated provirus. If the HIV long terminal repeat (LTR) is activated, tat protein is made from the proviral genome as an early gene product. Some of this tat protein activates viral gene expression and some activates the transcription of the multimerized TAR elements from the construct. As the multiple TAR RNA competes for tat binding, viral gene expression decreases. Since tat expression itself depends on the presence of tat, its expression will decrease along with all LTR directed gene expression until a certain equilibrium, dependent on the number of TAR elements in the multimer, is reached. This is the first time that a construct proposed for gene therapy use is under the control of biological regulation. The inhibitory gene product is expressed only if the cell becomes infected and tat is made. Otherwise, the construct is silent in the genome. Thus, since the constant antitat expression by the construct in normal cells will not occur, there is no long-term toxicity associated with expression of the construct in normal cells. Inhibition of viral replication using multiple TAR elements is effective against all HIV isolates because it is a functional inhibition. A significant problem associated with most HIV therapy and vaccines is the virus' high mutational rate. The efficacy of the present construct is not limited by retroviral mutations.

Accordingly, the present invention relates to a DNA construct encoding at least one copy, and preferably between 5 and 50 copies, and most preferably more than 20 copies, of the TAR element. Constructs to which the present invention relate comprise a DNA segment including multiple target response elements, such as TAR elements, a promoter, such as the HIV LTR, and vectors, such as pCD7 and retroviral vectors such as those derived from Murine Moloney Leukemia virus (MoMLV). The multiple activation response elements must be in tandem, or if separated, their transcription must not be interrupted by intervening sequences. Applicants discovered that HIV inhibition increased with the number of TAR elements until 25 TARs were present, at which point further increases in the number of TAR elements did not result in greater inhibition of HIV replication. This experiment was done in a transient expression assay system. In the case of stable integration in vivo, additional TARs will result in greater inhibition of HIV-1 replication since greater tat levels will be present.

In the constructs of the present invention, the promoter is operably linked to the multiple TAR DNA segment so that the promoter controls the amount of TAR RNA produced. While the following examples use the HIV-LTR and MoMLV LTR promoters, multiple TAR elements can be transcribed from various other promoters. For example, a promoter which can be activated by the tat protein might be used. Other promoters (e.g. CMV, SV40 or tRNA promoters) can be used; however, these promoters will constitutively express the gene product. The advantage to using promoters such as HIV-LTR is that they are inducible by the virus, providing greater specificity than can be obtained using other promoters. Further, tissue-specific promoters could be useful in these constructs.

The vector used in the constructs of the present invention must ensure high efficiency gene transfer to the in vivo target cell. Retroviral vectors are particularly preferred. Suitable vectors for use in the present invention include vectors which contain a replication origin and a selectable marker for propagation in prokaryotes. Vectors may contain more than one promoter. Further, vectors of the present constructs can contain sequences which allow the site-specific integration of the construct into the chromosome without disturbing cell function. The vectors can also contain "helper virus" sequences which allow transmission of the construct into the target cells and promote propagation of the vector through further infection.

Using the constructs of the present invention, the inventors have shown that the degree of down-regulation of HIV-1 gene expression is dependent on the number of TAR elements in the constructs. This indicates that several excess target nucleotide sequences can be used to down-regulate undesirable gene activity.

Combining TAR elements in tandem with other elements which inhibit viral expression is also a powerful method of inhibiting HIV replication. For example, the constructs of FIGS. 6, 8A, and 9A, made by the method of the present invention, were used to down-regulate HIV activity. Examples of appropriate elements for incorporation into the construct are transdominant regulatory proteins, antisense sequences, ribozymes directed against viral mRNA and coding sequences of antiviral agents such as interferons or immunostimulating agents. The inclusion of other activation or inhibition response elements is also contemplated.

The inhibitory activity of the poly TAR sequences was enhanced by including an antisense RNA directed against a critical HIV mRNA encoding the tat protein. It is also contemplated that the addition of other elements including a transdominant negative mutant of a viral protein (i.e. gag) in combination with poly TAR will also enhance the inhibitory activity of poly TAR. The constructs can also include a rev-response element (RRE). The RRE element of the construct functions to transport RNA made from the construct out of the nucleus into the cytoplasm.

The combination of TAR elements with a ribozyme against a viral mRNA or with an antisense RNA in a single construct provided two different types of inhibition. While TAR sequences inhibited HIV-1 directed gene expression by sequestering tat, the ribozyme inhibited protein translation by hybridizing to the target RNA and cleaving it and the antisense RNA inhibited tat translation by hybridizing to the viral mRNA thus preventing its association with ribosomes. Combining two inhibition mechanisms increased the potency of the method and led to almost total viral inhibition. The ribozyme used in the following examples, GAGNAM, is directed against gag mRNA, a particularly good target since it is conserved in the American HIV isolates. The antisense RNA was directed against the tat protein, another good target since tat is required to transactivate all HIV-1 gene transcription. In fact, the dual inhibition of tat with both poly TAR and antisense RNA resulted in virtually total inhibition of HIV-1 replication in immortalized and primary T-cells as well as in peripheral blood mononuclear cells (PBMC) isolated from AIDS patients. In addition, the antitat constructs protect $CD4^+$ cells from the cytopathic effects of HIV and promote expansion of the pool of $CD4^+$ T-cells. Further, PBMCs were protected for up to five months by introduction of the antitat construct.

Constructs containing TAR elements and transdominant mutants of HIV proteins, such as GAG, inhibit both HIV gene expression and viral assembly. The combination of TAR elements and mutant GAG provides pure functional inhibition which the virus cannot overcome by mutation.

The constructs of the invention can be made by various means known in the art, and should not be limited to only those cloning methods disclosed herein. The practitioner can prepare multiple target response sequences using purified response sequences which are then ligated in such a manner as to allow tandem addition of the sequences to provide multiple target response elements. It should be noted that, while constructs containing multiple activation response sequences have been exemplified, constructs can also contain multiple inhibitory response sequences, for example sequences which can sequester inhibitory proteins. Such constructs containing multiple inhibitory response sequences in tandem can be used, for example, to increase production of a desired product by stimulating the promoter responsible for expression of the desired protein.

The constructs of the present invention can be used in gene therapy by known methods. The method described by David Baltimore (*Nature* 335:395–396 (1988)) known as "intracellular immunization" can be used. For example, the constructs of the present invention can be introduced into bone marrow cells, including all hematopoietic stem cells. The blood cells can be either a mixed population or a homogenous population such as lymphocytes. Using the constructs exemplified, the cells of the HIV-infected individual would be used. After introduction of the gene, the cells would be injected back into the patient. To make space for the growth of the implanted cells, the marrow could be partially cleared by irradiation or with a medication before the modified cells are injected.

Peripheral blood cells from patients have been transduced with the antitat vectors of the present invention. As shown below, HIV infection in these cells was virtually abolished, and the cells were protected from further infection for five months. The cells containing the constructs are then reintroduced into the patient. In the treatment of HIV infection, the construct should be introduced into CD4+ cells. Since the turnover of these cells is relatively fast, reintroduction of the protected cells might be necessary so long as the viral infection is present.

The use of the multiple TAR element construct of the present invention is very advantageous. For example, the construct provides for specific inhibition of HIV-1 directed gene expression. The expression of the protective gene product is biologically controlled which is distinctively advantageous since constitutive expression of a TAR-containing transcript on normal cell processes in vivo may be deleterious. The usefulness of the construct is not limited by variability between different HIV isolates. Further, the use of the construct can be expanded by the downstream insertion of sequences such as ribozymes, antisense RNA or trans-dominant mutants of HIV proteins.

EXAMPLES

The following non-limiting examples are given to further describe the present invention. While the present invention is exemplified using HIV-1, SIV and the TAR element, one skilled in the art will appreciate that inhibition of other primate lentiviruses including HIV-2 can be expected to be effected using the method of the present invention.

Plasmid Construction

Plasmids containing different numbers of unidirectional TAR elements under the control of HIV-LTR were constructed. (See FIG. 2).

"Multimerized" TAR sequences were cloned downstream of the authentic TAR sequence of the 5' HIV-1-LTR deletion mutant CD7, lacking the negative regulatory element (NRE) and having higher level of expression as compared to the wild type HIV-1-LTR (Siekevitz et al, *Science* 238:1575–1578 (1987)). Plasmid pCD7 (kindly provided by Stephen Josephs) containing a part of the HIV-1 LTR (−278–+63) was digested with restrictions endonucleases and ligated with the multiple, tandem TAR elements. LTR-1TAR, LTR-4TAR and LTR-5TAR contained one, four and five copies of TAR elements, respectively.

For the construction of plasmids LTR-5TAR and LTR-4TAR, two oligonucleotides containing the sequence of the entire TAR element (+1 to +63) of HIV-1 flanked by half of the palindromic sequence for Dral and Smal restriction endonuclease recognition sites were synthesized. The oligonucleotides were purified, phosphorylated and annealed. The annealed DNA (TAR) was ligated in the presence of Dral and Smal allowing only tandem (directionally oriented) ligation of the TAR elements. Plasmid CD7-CAT (Siekevitz et al, *Science* 238:1575–1578 (1987)) containing a part of the HIV-I-LTR (−278 to +63) was digested with restriction endonucleases HindIII and NcoI, and the ends were filled in and ligated with the multiple tandem TAR elements. Of several *E. coil* strains tested, only one (Bj 5183: F, recBC, endol gal, met, str, thi, bio, hsd; kindly provided by F. Lacroute) was able to maintain these plasmids without rearrangements.

LTR-1-TAR was constructed by digesting CD7-CAT with HindIII and NcoI followed by filling in and religating the ends.

Two classes of control plasmids were generated: 5TAR having a deletion of the upstream promoter sequences (TAR sequences are present but not transcribed), and LTR-OTAR having no TAR sequences but containing the upstream promoter sequences (FIG. 2). LTR-OTAR was made by digesting CD7-CAT plasmid (Siekevitz et al, *Science* 238:1575–1578 (1987)) with Pvull and NcoI followed by filling in the ends and religation.

The 5TAR plasmid was constructed by deleting the 5' region of HIV-LTR from pLTR-5TAR by digestion with Xbal and Pvull followed by filling in the ends and religation. LTR-tat was constructed by digesting pSV-tat (Rappaport et al, *New Biol.,* 1:101–110 (1989a)) with SalI and BamHI, isolating the 350 bp tat-containing fragment and performing a blunt end ligation with CD7-CAT between HindIII and NcoI sites.

All constructs were confirmed by restriction mapping and sequencing.

The cloning strategy only allows the formation of direct repeats of the TAR element, since inverted repeats are cleaved by the SmaI and DraI enzymes during ligation. The correct orientation and secondary structure of each element is important to the desired inhibitory effect, since TAR functions in transactivation only in a position-dependent manner (Peterlin et al, *Proc. Natl. Acad. Sci. USA* 83:9734–9738 (1986)).

Down Regulation of Transactivation is Dependent on the Transcription of the TAR Elements To determine the effect of multiple TAR elements on HIV-LTR directed gene expression, TAR expression plasmids were cotransfected with LTR-CAT (Siekevitz et al, *Science* 238:1575–1578 (1987)) and LTR-tat or pSV-tat (Rappaport et al, *New Biol.,* 1:101–110 (1989a)) in COS cells.

COS-1 cells were grown in Dulbecco's Modified Eagle Medium (DMEM) supplemented with 10% fetal calf serum (GIBCO). $2\times10^5$ cells were plated in 3 ml media in 6 well tissue culture plates one day prior to transfection. 25 μg of total plasmid was used for 3 wells. The amounts of the different plasmids are indicated in the figures. Plasmid pBR322 was used as carrier DNA. Transfections were carried out by calcium phosphate precipitation (Chen and Okayama, *Mol. Cell. Biol.* 7:27–45 (1987)). 48 hours after transfection, cells were collected (cell remover reagent; Sigma, St. Louis, Mo.), and crude cellular extracts were made in PBS.

The plasmid RSV-Luciferase was included as an internal control to detect the transfection efficiency. The amount of CAT protein and relative levels of luciferase activity were determined from extracts of transfected cells. CAT protein was assayed with an ELISA kit (5 prime-3 prime, Boulder, Colo.) according to the manufacturer's instructions. Luciferase activity was measured according to Stanley and Williams (*Anal. Biochem.* 29:381, (1969) and activities were expressed in arbitrary units (ARU).

As shown in FIG. 3A, multiple TAR elements transcribed from HIV-LTR inhibited HIV-LTR directed gene expression in the presence of tat and the down regulation observed was proportional to the number of TAR elements in the construct. LTR-4TAR and LTR-5TAR inhibited transactivation an average of 70% and 80%, respectively. LTR-1TAR also had a measurable effect, resulting in up to 40% down regulation. This reduction represents a cumulative effect of the inhibition of both CAT and tat expression, since both gene products are under the control of the HIV-I-LTR in this experiment. Multiple TAR elements also suppressed transactivation when tat was expressed constitutively from the SV40 late promoter (FIG. 3B), albeit at a reduced level. Results presented in FIGS. 2A and B illustrate that CAT expression is reduced 82% when tat is expressed from HIV-1 LTR compared to a 50% reduction observed with the constitutively expressed tat.

Transcription of the multimerized TAR sequence is required for efficient down regulation and accumulation of steady state competitor RNA which occurs only in the presence of tat (See FIG. 3C). Sequences upstream of the TAR element cannot account for the observed effect. The LTR-OTAR plasmid containing no TAR sequences or the 5TAR plasmid having a deletion of the upstream promoter sequences, produced no significant effect on HIV-1 LTR directed gene expression (See FIGS. 3A, 3B, 3C).

Figure 3D:
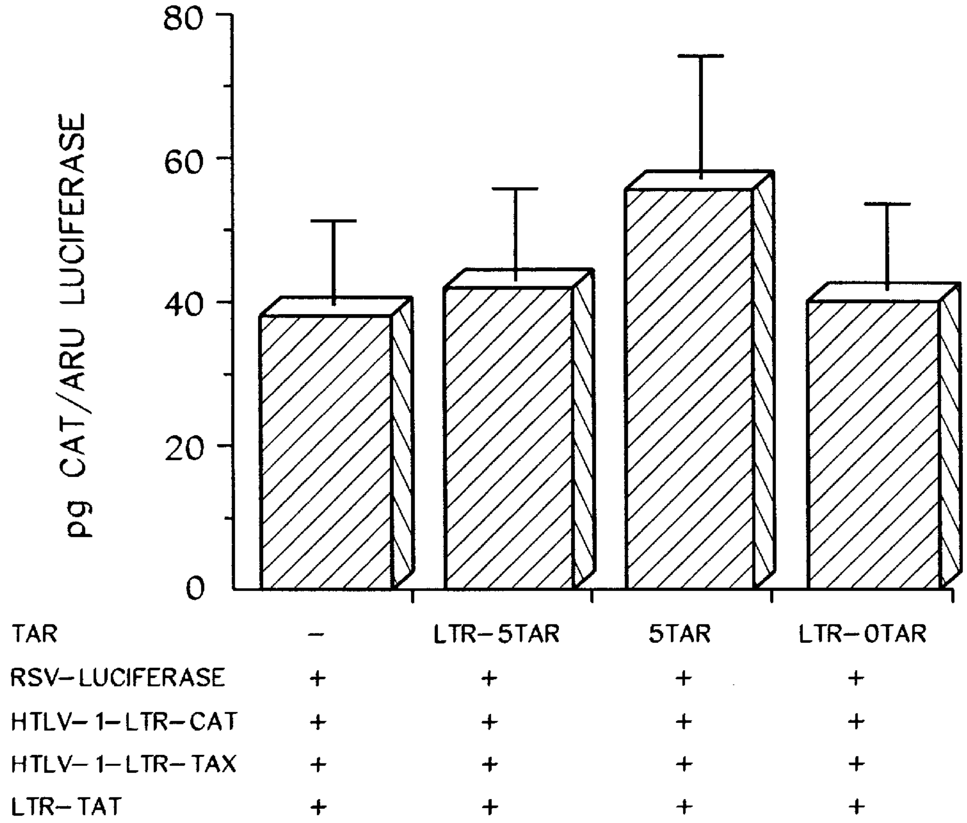

Cotransfection of COS cells was performed with a different human retroviral LTR to determine the specificity of the effect of multimerized TAR RNA. HTLV-I-LTR-CAT (kindly provided by M. Nerenberg) was used as a reporter gene and HTLV-I-LTR-TAR plasmid was included as a transactivator of the HTLV-I LTR (Sodroski et al, *Science* 225:381–385 (1984); Felber et al., *Science* 229:675–679 (1985)). LTR-tat was also supplied for the transcription of the multimerized TAR elements. The results indicated that the expression of multiple TAR RNA elements did not affect HTLV-I promoter activity (FIG. 3D), suggesting that down-regulation of gene expression is specific to the HIV-LTR.

FIG. 3 also demonstrates that the multiple TAR RNA elements can specifically inhibit transactivation of HIV gene expression. The RSV-luciferase construct was used to verify that the specificity of the multiple TAR RNA elements did not affect the use of heterologous promoters. No significant differences in RSV promoter activity could be detected with TAR RNA or DNA elements. This indicated the relative promoter activities of the HIV-LTR versus RSV promoter as the proportion of CAT and luciferase expression.

Inhibition of the Transactivation Parallels the Amount of TAR Transcripts

LTR-CAT and LTR-tat were cotransfected with increasing amounts of LTR-5TAR to determine the effect of different amounts of TAR transcripts on tat-mediated transactivation. RNA was isolated using CINNA/BIOTEX RNAzol reagent according to the manufacturer's protocol. For Northern analysis, RNA was electrophoresed through a 1% formaldehyde/agarose gel, transferred onto nitrocellulose paper and hybridized with a nick-translated $^{32}P$-labeled probe as previously described (Maniatis et al., *Molecular Cloning: A Laboratory Manual,* Cold Spring Harbor Laboratory Press, Cold Spring Harbor, N.Y. (1982)).

FIG. 4A illustrates that increasing the amount of LTR-5TAR plasmid resulted in a proportional decrease in CAT expression (up to 97%). Inhibition cannot be due to the competition for limiting transcription factors which associate with the HIV-I LTR since the amount of transfected LTR upstream sequences was kept constant in this experiment. Increasing amounts of transfected LTR-5TAR plasmid resulted in a similar increase in LTR-5TAR transcripts (FIG. 4B). From these experiments, it was concluded that down-regulation of HIV-1 LTR directed gene expression was dependent upon the relative amount of expression plasmid DNA introduced into cells, in addition to the number of transcribed TAR elements contained in the expression plasmid.

Figure 4C:
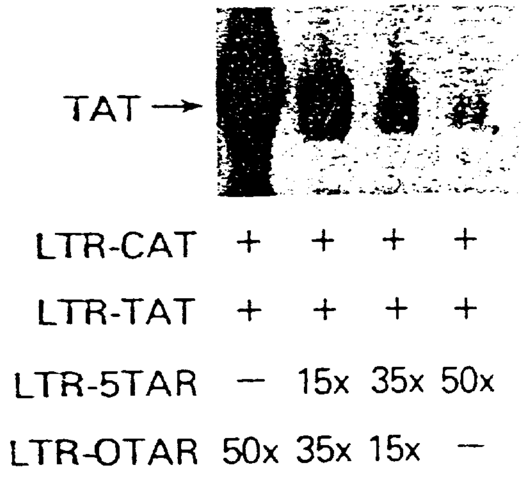

Northern blots showed that tat and CAT expression appeared to be reduced in parallel by multimerized TAR RNA (FIG. 4C), which was expected since they are both driven by HIV-LTR.

The data of FIG. 4 support the teaching that the down regulation of gene expression is dependent on the number of transcribed target activator nucleotide sequences. HIV-1 transactivation by tat can be down regulated by up to 97% using 5 TAR elements in tandem, and this down regulation is a function of the amount of TAR RNA transcription. The data suggest that a construct containing more than 5TAR elements would provide an even more pronounced inhibitory effect.

Constructs Containing More than 5 TAR Elements

The multiple TAR construct was expanded and plasmids containing up to 50 TAR elements were constructed and tested (FIG. 5).

pSPT18-polyTAR constructs containing between 15 and 45 TAR were constructed by cutting a pSPT18 vector (Pharmacia) with Xbal. The ends were then blunt-ended with the large fragment of DNA polymerase I (Klenow fragment) and dephosphorylated. The insert was prepared by cutting pLTR- 5TAR with Pvull and Scal and isolating the 5TAR-containing 455 base pair fragment.

The above vector and insert were then ligated and used to transform *E. coli.* Plasmid DNA was prepared from single colonies and clones containing large inserts were selected using methods well known in the art. The orientation of the insert was checked with restriction enzyme digestion using Sspl and HindIII+Sspl.

LTR-5TAR-CAT was cloned as follows. The LTR-CAT vector was cut with Xbal+HindIII and larger fragments were isolated. The insert LTR-5TAR fragment, prepared by the polymerase chain reaction (PCR), was prepared by cutting the PCR fragment with Xbal+HindIII. The vector and insert were ligated and used to transform *E. coli.* Single colonies were checked for the presence of the plasmid.

LTR-46TAR was prepared by cutting LTR-CAT with HindIII+BamHI and isolating the larger fragment containing the LTR-1TAR+pBR322. pSPT45TAR, prepared as described above, was cut with HindIII+BamHI and the larger fragment containing the 45TAR was isolated. The isolated fragments were ligated and *E. coli* were transformed with the ligated product.

LTR-25TAR and LTR-50TAR were also prepared. Vector LTR-5TAR-CAT was cut with SalI+BamHI and the fragments containing the LTR-5TAR+pBR322 were isolated. pSPT-20TAR or pSPT-45TAR were cut with SalI+BamHI and fragments containing the 20TAR or the 45TAR were isolated. The vector and insert were then ligated and *E. coli* were transformed with the ligated product.

The results depicted in FIG. 5 show that inhibition of HIV-1 LTR-directed gene expression increased with the number of TARs in the construct until 25 TARs were used. Increasing the number of TARs above 25 did not increase the inhibition. Thus, it is believed that the tat protein became saturated at this point. It is also possible that this test was not sensitive enough to detect further increases in inhibition.

Construction of Ribozyme-Poly-TAR

For the construction of pRRE-ribozyme, the vector pRRE (Daefler et al, *Proc. Natl. Acad. Sci USA* 87:4571–4575 (1990)) containing the RRE (rev-response element under the control of a T7 promoter) was cut with BamHI, dephosphorylated and purified. The insert, a 65 bp long ribozyme PCR fragment (Chang et al, *Clin. Biotechnol.* 2:23–31 (1990)) flanked by BamHI sites was cut with BamHI and purified. This ribozyme is directed against HIV-1 GAG mRNA (Sarver et al., (1990) *Nature,* 247:1222).

The vector and insert were ligated and an aliquot of the ligation mix was used to transform *E. coli.* Plasmids were prepared from individual transformants and tested by restriction enzyme digestion. Eight clones were found to contain the insert. These clones were tested in vitro for biological activity and 3 of the 8 clones were found to have the ability to cut a synthetic substrate (substrate gift of J. Rossi).

The 65 base pair HIV-1 gag-specific ribozyme was subcloned into the BamHI site of pRRE (Chang et al., (1990) *Clin. Biotechnol.,* 2:23–31) by standard techniques. The orientation of the ribozyme in the pRRE-ribozyme construct was confirmed by an in vitro cleavage reaction. The 4.6 kilobase XbaI fragment isolated from LTR-50TAR was inserted into the SnaBI site of the DC retroviral vector (Hantzopaulos et al, (1989) *Proc. Natl. Acad. Sci. USA,* 86:3519) to generate the DC-LTR-50TAR construct. The RRE-ribozyme fragment was isolated from pRRE-ribozyme and after HindIII and EcoRI digestion and cloned into the ScaII site of DC-LTR-50TAR. The resulting construct DC-LTR-50TAR-RRE-ribozyme was designated TAR-Rib (FIG. 6). The DC retroviral vector will allow high efficiency gene transfer. Other vectors which ensure high efficiency gene transfer would also be appropriate for use in the present invention.

Construction of ΔGAG-Poly-TAR pRRE-ΔGAG was constructed by cutting the pRRE vector with BamHI, dephosphorylating the ends and purifying the vector. The ΔGAG protein encoded by the mutant viral DNA HT4(VI-ΔE-dhfr) (Torno et al., *Cell* 59:113–120 (1989)) can dominantly interfere with the replication of HIV-1. Plasmid DNA HT4(VI-ΔE-dhfr) was cut with BglII and a 1429 Bp fragment containing ΔGAG was isolated from a 1 % agarose gel. The vector and insert were 5 ligated and an aliquot of the ligation mix was used to transform *E. coli.* Plasmids were prepared from individual transformants and were tested by restriction enzyme digestion using EcoRI+SphI.

For construction of LTR-polyTAR-RRE-ΔGAG (FIG. 7), the vector LTR-46TAR is cut with SalI and the ends filled in with the Klenow enzyme. The DNA is then purified. For the preparation of the insert, pRRE-ΔGAG is cut with EcoRV and SmaI, the 1.6 kb fragment is isolated by agarose gel electrophoresis and the vector and insert are ligated and used to transform *E. coil.* Individual colonies are checked. The construct is inserted into the DC-vector as described above.

A plasmid designated LTR-7TAR was deposited in *E. coli* at the American Type Culture Collection in Bethesda, Md. on Jan. 17, 1990 under the accession number 68203. Further, the LTR-50TAR plasmid was deposited in *E. coli* at the American Type Culture Collection in Bethesda, Md. on Oct. 12, 1990 under the accession number 68446. The plasmids were deposited under the terms of the Budapest Treaty.

Transduction of COS-1 Cells with Antitat Constructs

The antitat gene was cloned by ligation of the HIV-1 LTR and the antisense Tat II gene (AS-TAT; Chang et al., (1994) *Gene Therapy, in press). pLTR-*25TAR was digested with BamHI, blunt-ended and ligated to the blunt-ended AS-TAT PstI DNA fragment (Lisziewicz et al., (1993) *Proc. Natl. Acad. Sci. USA,* 90:8000–8004; FIG. 8A). The LTR-25TAR-ASTAT (antitat gene) cassette was inserted into the 3'-LTR of the replication deficient double copy retroviral vector G3 in both orientations using blunt-end ligation. The structure of the antitat retroviral vector plasmids was confirmed by restriction analysis. Antitat inhibits tat function in two ways. The poly-TAR RNA binds and sequesters the tat protein in the nucleus and the antisense tat RNA inhibits the translation of tat mRNA in the cytoplasm. Tat produced by the provirus or taken up by the cell activates transcription of viral and antitat RNA. However, antitat RNA ultimately decreases the amount of tat protein, resulting in diminished proviral activation and downregulation of the antitat gene (FIG. 8B). This activation and inhibition leads to an equilibrium between tat and antitat; thus, neither tat not antitat can be overexpressed due to this autocrine regulation.

To demonstrate inhibition of tat transactivation, COS-1 cells (ATCC CRL 1650) were transduced with different plasmids using liposome-mediated gene transfer (Lipofectin™; Boehringer Mannheim, Indianapolis, Ind.) carried out according to the manufacturer's protocol. COS-1 cells were transduced with 2 $\mu$g pLTR-CAT as a reporter of HIV-1 gene expression, 0.7 $\mu$g pLTR-TAT as a source of transactivator (Lisziewicz et al., (1991) *New Biol.,* 3:82–89) and 1 $\mu$g of the inhibitory or control plasmid. CAT activity was determined as described (Neumann et al., (1987) *BioTechniques* 5:444).

The results indicate that LTR-25TAR inhibited tat transactivation by 81%, AS-TAT inhibited transactivation by 23%, while the dual function antitat gene exhibited 94% inhibition (FIG. 8C). A similar result to that obtained with the dual function construct (90% inhibition) was observed when cells were cotransduced with the LTR-25TAR and AS-TAT plasmids, indicating that the combination of two tat inhibitory genes has an additive effect in blocking HIV-1 gene expression. This demonstrates that the activity of the antitat gene depends on both the poly TAR and AS-TAT RNA components.

To determine whether the inhibitory constructs could prevent HIV-1 replication, the constructs were transduced into T-cells as described below.

Gene Transfer and HIV Infection of Immortalized T Cells

Antitat retrovirus vector plasmids were linearized with NdeI to induce integration outside the retrovirus vector cassette and to avoid deletions or rearrangements during the packaging of the retroviral vector particles. Linearized plasmids were transduced into the PA317 murine amphotropic packaging cell line (ATCC CRL 9078; Miller et al., (1986)

*Mol. Cell. Biol.,* 6:2895–2902) and G418-resistant cell colonies were selected and pooled. Cell supernatants containing infectious retroviral particles were used to transduce cells. To verify the integrity of the antitat gene, genomic DNA was isolated, digested with KpnI and analyzed by electrophoresis on a 1 % agarose gel. The gel was blotted onto nitrocellulose followed by detection with a $^{32}$P-labeled probe complimentary to TAR RNA (5'-GCTCCCAGGCTCAGATCT-3'; SEQ ID NO: 1). The antitat minigene was inserted into the Murine Moloney Leukemia Virus-derived vector G1 (McLachlin et al., (1993) *Virology,* 195:1–5) in both the forward (DC-antitat/30) and reverse (DC-antitat/23) orientations (FIG. 9A). These constructs were stably transduced into PA317 cells and infectious retroviral supernatants were used to evaluate the efficacy of antitat genes transferred into immortalized primary lymphocytes. Southern blot analysis of transfected cell DNA demonstrated the preservation of the structure of the introduced plasmids.

The CD4$^+$ Molt3 T-cell line (ATCC CRL 1552) was transduced with retroviral supernatants and G418 resistant cell populations were selected without single cell cloning. These cells were challenged with HIV-1/HTLV-IIIB at multiplicities of infections (MOI) of 1, 0.1 and 0.01. Virus replication was monitored by the p24 antigen-capture assay (Coulter, Hialeah, Fla.) and viable cell numbers determined as described by Pauwels et al. (*J. Virol. Methods,* 20:309–321, 1988). For long term inhibition assays, cells were cultured in RPMI supplemented with 15% fetal calf serum (FCS) and G418 for several months.

At a MOI=1, HIV-1 replication was blocked for up to seven days (FIG. 9B). At this MOI, no difference was observed in inhibition promoted by the forward and reverse oriented antitat vectors (97% and 96% inhibition, respectively). The G1 control vector lacking an antitat gene did not exhibit antiviral activity. As the MOI was decreased 10 and 100 fold (MOI=0.1 and 0.01; FIGS. 9C and 9D, respectively), viral replication was blocked for up to 40 days for the forward vector and up to 14 days for the reverse vector. For MOI=0.1, the greatest inhibition was detected 10 days after infection. Both antitat vectors blocked HIV-1 replication by about 98% For MOI=0.01, the highest level of inhibition by DC-antitat/23 (97%) was detected 14 days after infection. This level of inhibition was also promoted by DC-antitat/30, although this vector maintained this inhibition for 31 days after infection. This indicates that the antiviral effect of these vectors may be more pronounced at the early stages of HIV-1 infection when the MOI (viral burden) is lower. To determine whether the antiviral effect mediated by antitat persisted over a longer period of time, Molt3 cells were analyzed as described below.

Long-term antiviral effect of the antitat gene

Figure 10B:
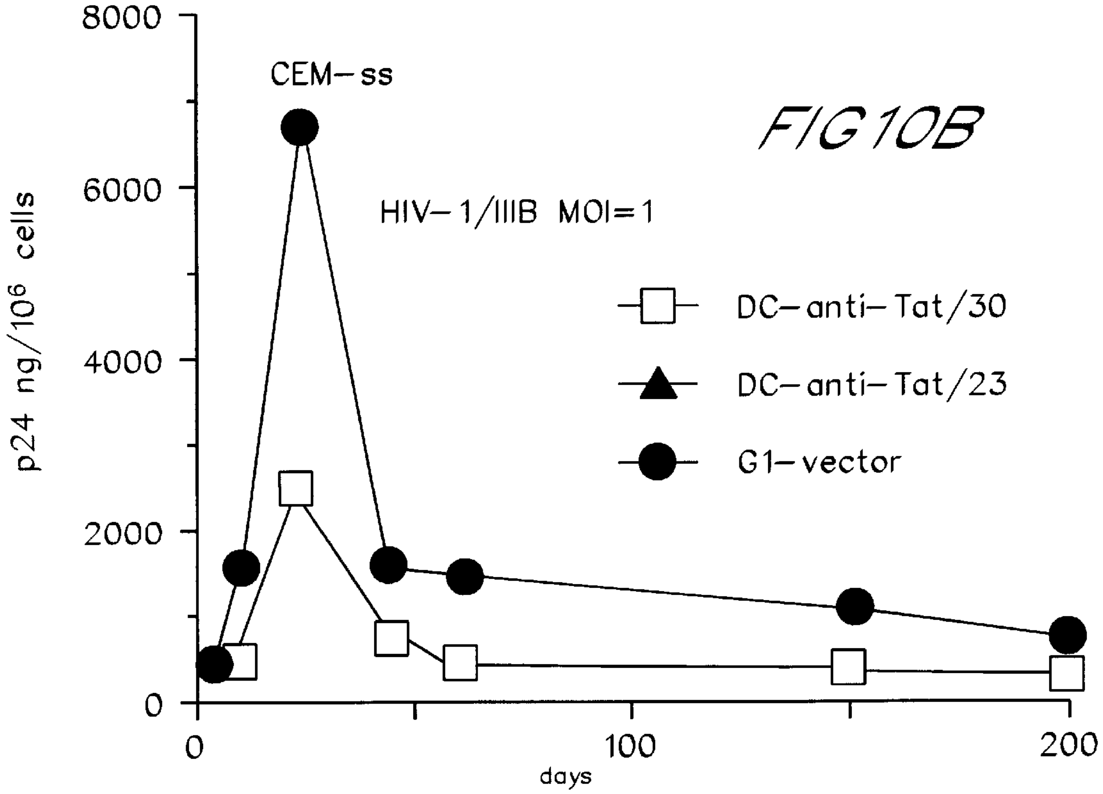

The long term antiviral effect of the antitat gene was evaluated in transduced Molt3 cells infected with HIV-1/HTLV-IIIB at a MOI=1. Antiviral activity persisted for up to 5 months which was the termination time of the experiment (FIG. 10A). Although cells transduced by both antitat and control vectors produced p24 soon after HIV-1 infection, the levels were 20 to 30 fold lower in antitat transduced cells than in cells transduced with the control vector. The viability of the antitat protected cells was comparable to the uninfected ones in contrast to the massive syncytia formation and death of the control HIV-1 infected cells. Importantly, antitat transduced cells were alive and maintained a normal histological appearance five months after HIV infection. At this time, very low but detectable levels of p24 were measured, consistent with the expected autocrine control of antitat gene expression. Therefore, the regulatory interactions between tat and antitat was sufficient to control viral replication for several months in Molt3 cells even after high viral challenge. Comparable results were obtained using another CD4$^+$ T-cell line, CEM-SS (ATCC CCL 119; FIG. 10B), although these cells were not killed after high MOI challenge. Initially, only a five fold inhibition was observed; however, after 200 days it exceeded 3000 fold. These results emphasize that the antitat gene is effective in long term HIV-1 inhibition.

The antiviral efficacy of antitat was then evaluated in activated, primary peripheral blood mononuclear cells (PBMC) as described in the following example.

Inhibition of Viral Replication in PBMCs

PBMC were isolated from the peripheral blood of normal donors by Ficoll/Hypaque density gradient centrifugation, activated by phytohemagglutinin P (PHA-P; Difco, Detroit, Mich.) and cultured in RPMI containing 15% FCS and 5% interleukin-2 (IL-2, Boehringer Mannheim). After two days in culture, aliquots of PBMC ($10^6$ cells/ml) were transduced with retroviral supernatants as described above and selected with G418 (250 and 500 $\mu$g/ml) for 10 days. After 2 days, cells were infected with HIV-1/HTLV-IIIB and viral replication was monitored by a p24 antigen capture ELISA (Coulter) and viable cell number determination (Pauwels et al, 1988).

Antitat inhibited HIV-1/HTLV-IIIB replication in primary lymphocytes (FIG. 11A), similar to the results obtained with immortalized lymphocyte cell lines (FIG. 9C). The forward antitat vector construct was a more effective inhibitor of HIV-1 replication in PBMCs than was the reverse-oriented construct, although this was apparent only at a MOI=0.01 similar to Molt3 cells. At lower HIV-1 challenge (MOI=0.001), the antiviral activity of both antitat vectors was the same and resulted in complete inhibition of HIV-1 replication (p24 undetectable 25 days after infection) compared to a control vector (281 $\mu$g p24/$10^6$ cells; FIG. 11C). These results support the validity of using Molt3 cells for initial preclinical biological efficacy evaluations of HIV-1 inhibitory gene transfer. The complete inhibition of HIV-1 replication in primary cells also confirms that the antiviral activity of the antitat gene is more efficient at lower viral challenge.

The antitat gene not only blocked HIV-1 replication, but also protected CD4$^+$ lymphocytes from the cytopathic effect of the virus. Antitat and control vector-transduced primary lymphocytes were selected and infected with HIV-1/HTLV-IIIB. CD4 and CD8 subsets were analyzed by flow cytometry three weeks after virus infection using 2 $\mu$g/ml fluorochrome-labeled monoclonal antibodies to CD4 and CD8 (Becton Dickinson, San Jose, Calif.). The antitat gene protected CD4$^+$ cells in contrast to the G1 control vector where the majority of CD4$^+$ cells were killed (FIG. 11B). Thus, antitat not only inhibited HIV-1 replication and virus spread, but also prevented the killing of CD4$^+$ lymphocytes.

To verify the enrichment through G418 selection of transduced primary PBMCs, genomi1c DNA was isolated from the transduced cells before and after G418 selection. PCR standards were prepared by mixing (0–30%) genomic DNA isolated from the G1 vector producer cell line PA317 (containing one copy of the neomycin phosphotransferase gene per cell) with genomic DNA isolated from PA317 cells. Standard PCR reactions were performed using primers complementary to the neo gene. The start points of these primers corresponded to nucleotides +45 (5'-GGTGGAGAGGCTATTCGGCTATGA-3'; SEQ ID NO: 2)

and +444 (5'-ATCCTGATCGACAAGACCGGCTTC-3'; SEQ ID NO: 3) of the neo gene. Under the experimental conditions, the efficiency of transduction of activated PBMCs was between 0.3–5% before selection and 30% after selection The antiviral activity of antitat was then evaluated using a primary clinical HIV-1 isolate as described below.

Efficacy of Antitat in Inhibiting a Primary HIV Isolate

In addition to the experiments described above using a "laboratory" strain of HIV-1, a primary clinical HIV-1 isolate was used (strain No. 3935, kindly provided by Drs. R. Redfield, Walter Reed Army Institute of Research, Rockville, Md. and P. Markham, Advanced BioSciences, Kensington, Md.). This isolate was never grown in immortalized cell lines, only passaged in primary PBMCs. Normal PBMCs were transduced with antitat or control vectors, selected in G418 and infected with HIV-1/3935. Both forward and reverse orientation antitat vectors inhibited HIV-1/3935 replication by more than 2000 fold in primary lymphocytes (FIG. 11C). These results indicate than antitat gene therapy is not limited to a particular laboratory HIV-1 strain, but is capable of blocking replication of "field" isolates of HIV obtained from infected individuals.

To determine the efficacy of antitat inhibition of established HIV-1 infection, PBMCs from AIDS patients were transduced with replication-deficient retroviral vectors containing the antitat gene as described below.

Inhibition of Established HIV-1 Infection by Antitat

PBMCs were isolated from peripheral blood of AIDS patients and normal donors, activated with PHA-P and cultured in the presence of IL-2. Activated cells were transduced repeatedly with the antitat or control vectors, expanded with IL-2 for 9–14 days in the absence of selection and analyzed for HIV-1 replication. The first PBMCs were isolated from patient Li (absolute CD4 count=2/mm$^3$). Nine days after PHA activation, cells transduced with the control vector or untransduced cells formed syncytia and the majority of cells died. In contrast, no syncytia were observed in the antitat transduced cells and most of these cells were viable. Viral replication was measured by p24 antigen capture and flow cytometry of CD4 and CD8 cell surface antigens. Cells transduced with the antitat gene exhibited a 3000 fold reduction in viral replication compared to control cells (FIG. 12A). In addition, six times more CD4$^+$ cells were observed in antitat transduced cells compared to control vector transduced cells (FIG. 12B). Further, the CD4/CD8 ratio was significantly higher in antitattransduced cells compared to either untransduced cells or control vector transduced cells. Thus, antitat effectively inhibited a highly virulent HIV-1 variant and protected virus-induced killing of CD4$^+$ cells from an AIDS patient.

The effect of antitat on HIV-1 replication was also assessed in other AIDS patients. Significant amounts of virus production was detected in only one of these patient's cells (patient D). Unmodified and control vector transduced cells produced 20 times more virus than antitat transduced cultures (FIG. 13A). Similar to patient Li, significantly more CD4 cells were present in antitat transduced cultures than in control treated cultures (FIG. 13B).

Even in PBMCs of AIDS patients not exhibiting notable virus production, expansion of antitat transduced CD4$^+$ lymphocytes was observed compared to controls (Table 1). A significant increase was also observed in the relative ratio of CD4/CD8 cells. The expansion of CD4$^+$ cells was dependent on the relative number of CD4$^+$ cells in the culture. Even in PBMCs of AIDS patients not exhibiting notable virus production, expansion of antitat transduced CD4$^+$ lymphocytes was observed compared to controls (Table 1). A significant increase was also observed in the relative ratio of CD4/CD8 cells. The expansion of CD4$^+$ cells was dependent on the relative number of CD4$^+$ cells in the culture.

To mathematically analyze these experiments, a parameter called the CD4% reconstitution factor (CRF) was designated which is defined as the ratio of CD4% of cells transduced with the antitat gene to the CD4% of cells transduced with the G1 control vector (Table 1). The CRF defines the relative effectiveness of an ex vivo gene therapy treatment of a given patient and depends on the viral burden, efficacy of the inhibitory gene and efficacy of the inhibitory gene delivery system. The CRF does not depend on the viral genotype if the inhibitory gene is a general inhibitor of all HIV-1 variants as is antitat. The CRF increases as the CD4$^+$ T-cell number of the patient decreases, suggesting that antitat can prevent the death of infected cells. With increasing CD4$^+$ T-cell count, the CRF approaches 1, indicating that ex vivo gene therapy would mostly target uninfected, healthy cells. In the case of asymptomatic or healthy individuals, the CRF is 1, indicating an intact peripheral hematopoietic system.

FIG. 14 describes the CRF as a function of the number of CD4$^+$ T-cells, which can be mathematically approached by a third degree equation. The data were calculated using cells isolated from different patients and healthy donors. The constants of the equations (FIG. 14) establish that the maximal effectiveness of these vectors do not depend on the characteristics of a particular patient's virus or cells. The maximal effectiveness of DC-antitat/23 (2.7) was only 82% of DC-antitat/30 (3.3), confirming that DC-antitat/30 is a more effective vector. Thus, this type of experiment and CRF calculations may be used to characterize other approaches for HIV-1 targeted gene therapy.

TABLE 1

| Patient | vector | CD4 | CD8 | CD4/CD8 | CRF |
|---|---|---|---|---|---|
| B | — | 14.6 | 84.1 | 17.4 | — |
| B | G1 | 12.4 | 86.6 | 14.3 | — |
| B | DC-antitat/30 | 22.4 | 78.2 | 28.6 | 1.8 |
| B | DC-antitat/23 | 18.0 | 81.0 | 22.2 | — |
| L | — | 11.7 | 81.0 | 14.4 | — |
| L | G1 | 9.5 | 80.3 | 11.8 | — |
| L | DC-antitat/30 | 22.5 | 55.8 | 40.3 | 2.4 |
| L | DC-antitat/23 | 15.8 | 70.8 | 22.3 | 1.7 |
| H | — | 26.7 | 65.7 | 40.6 | — |
| H | G1 | 30.6 | 65.7 | 46.6 | — |
| H | DC-antitat/30 | 36.2 | 49.5 | 73.2 | 1.2 |
| H | DC-antitat/23 | 33.7 | 48.9 | 69.0 | 1.1 |
| D | — | 1.7 | 94.5 | 1.8 | — |
| D | G1 | 1.6 | 94.6 | 1.7 | — |
| D | DC-antitat/30 | 5.7 | 94.5 | 6.0 | 3.6 |
| D | DC-antitat/23 | 5.2 | 95.8 | 5.5 | 3.2 |
| Li | — | 1.9 | 94.1 | 2.0 | — |
| Li | G1 | 1.0 | 94.3 | 1.0 | — |
| Li | DC-antitat/30 | 5.7 | 97.0 | 5.9 | 5.7 |
| Li | DC-antitat/23 | nd | nd | nd | — |
| ND/1 | — | 71.7 | 25.1 | 285.2 | — |
| ND/1 | G1 | 71.0 | 24.9 | 284.9 | — |
| ND/1 | DC-antitat/30 | 67.3 | 31.5 | 213.7 | 0.9 |
| ND/1 | DC-antitat/23 | 66.6 | 31.6 | 210.7 | 0.9 |
| ND/2 | — | 57.5 | 39.8 | 144.5 | — |
| ND/2 | G1 | 53.9 | 43.3 | 124.5 | — |

TABLE 1-continued

| Patient | vector | CD4 | CD8 | CD4/CD8 | CRF |
|---|---|---|---|---|---|
| ND/2 | DC-antitat/30 | 53.5 | 45.5 | 117.7 | 1 |
| ND/2 | DC-antitat/23 | 53.3 | 42.7 | 124.7 | 1 |

CRF = CD4% of antitat/CD4% of G1
ND = normal donor
nd = not detected

To determine whether $CD4^+$ T-cell expansion was due to specific inhibition of HIV-1 induced cytopathic effect and not to nonspecific effects of the antitat gene, PBMCs isolated from healthy donors were transduced with either antitat or control vectors. As expected, the percentage of $CD4^+$ T-cells and the CD4/CD8 ratio was much higher than in cells from AIDS patients and no expansion of antitat transduced $CD4^+$ T-cells was observed compared to controls. These results suggest that the antitat gene prevents the cytopathic effect of HIV-1 on PBMCs from AIDS patients. In addition, antitat not only rescued infected T-cells, but promoted their expansion in culture. Importantly, these results demonstrate that antitat treatment is effective for established as well as de novo HIV-1 infections.

In summary, the antitat gene has several features relevant to its therapeutic potential. First, since antitat expression is dependent on activation by tat, the antitat gene should only be expressed in cells containing the tat protein (e.g. HIV-infected cells). In addition, since antitat also inhibits tat, the inappropriate overproduction of the inhibitory RNA in uninfected cells will not occur. Reintroduction of blood cells transduced with antitat would therefor provide the patient with a set of HIV-1 resistant cells. Transduction of bone marrow stem cells by methods known to those of skill in the art with antitat would provide the patient with an ongoing complement of HIV-1 resistant cells. This treatment is expected to increase the number of viable T-cells in an AIDS patient by inhibiting the in vivo expansion of HIV-1. Second, antitat inhibits tat function through two different mechanisms which have additive inhibitory effects. Since Tat activates HIV-1 gene expression and the production of inflammatory cytokines (Buonaguro et al., (1992) *J. Virol.,* 66:7159–7167), reduction in tat levels will also inhibit cytokine activation. Third, since there is a low likelihood of simultaneous tat and TAR mutation during viral replication and due to the conserved structural requirements for tat-TAR interaction, viral escape is less likely than with some other gene therapy approaches. In fact, poly TAR is a general inhibitor of primate lentiviruses, inhibiting not only HIV-1, but also the distantly related simian immunodeficiency virus ($SIV_{mac\ 251}$) as described by Lisziewicz et al., (1993) *Proc. Natl. Acad. Sci. USA,* 66:8004–8008). This is described briefly below.

Inhibition of SIV Replication by Poly TAR

TAR-Rib, described hereinabove, was transfected into the GPe86 ecotropic packaging cell line (Markowitz et al., (1988) *J. Virol.,* 62:1120–1124). After 72 hours, the cell-free supernatant was used to infect the GP+envAm12 amphotropic packaging cell line (Markowitz et al., (1988) *Virology,* 167:400–406). Three days later, cells were split and G418-resistant colonies were selected to produce infectious retrovirus.

TAR-Rib and DC vector-transduced Molt3 cells ($1\times10^8$ cells) were treated with 20 $\mu$g DEAE-dextran, washed and infected with $SIV\text{-}1_{mac251}$ at a low MOI ($ID_{50}$=0.5) for 2 hours at 37° C. Cells were washed and maintained in RPMI 1640 containing 10% FCS. Supernatants were collected and assayed for SIV-1 p27 using an ELISA (Coulter). Up to 90% inhibition of SIV replication was observed in the TAR-Rib-transduced cells compared to the vector alone (FIG. 15). In addition, flow cytometry analysis using monoclonal antibodies to CD4 indicated that 92% of the SIV-infected, TAR-Rib-transduced cells expressed CD4 on their surface. In contrast, only 52% of the SIV-infected, DC vector-transduced cells expressed CD4. Thus, The TAR-Rib construct was able to protect cells against the loss of CD4. The inhibition of SIV replication and CD4 protection described above is only due to the 50 TAR elements, since the gag ribozyme has no specificity for SIV mRNA.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A DNA construct comprising a vector and a promoter operably linked to a plurality of DNA segments encoding Human Immunodeficiency Virus-1 (HIV-1) tat activation (TAR) elements so that said elements are transcribed in tandem, wherein said plurality is a number between 5 and 50.

2. The DNA construct according to claim 1, wherein said promter is primate lentivirus long terminal repeat (LTR) promoter.

3. The DNA construct according to claim 2, wherein said primate lentivirus LTR is the Human Immunodeficiency Virus-1 (HIV-1) LTR.

4. The DNA construct according to claim 1 having 25 TAR elements.

5. The DNA construct according to claim 1, wherein said promoter is regulated by HIV-1 tat protein.

6. The DNA construct according to claim 1, wherein said vector is pCD7.

7. The DNA construct according to claim 1, wherein said vector is a retroviral vector.

8. The DNA construct according to claim 1, wherein said DNA construct is deposited as *Escherichia coli* LTR-7TAR, Bj, rec B- in the American Type Culture Collection (ATCC) under the accession number 68203.

9. The DNA construct according to claim 1 further comprising a sequence encoding a ribozyme that inhibits lentivirus replication.

10. The DNA construct according to claim 1 further comprising a sequence encoding an antisense that inhibits lentivirus replication.

11. The DNA construct according to claim 1 further comprising a sequence encoding a transdominant negative mutant viral protein that inhibits lentivirus replication.

* * * * *

SEQUENCE LISTING

```
(1) GENERAL INFORMATION:

   (iii) NUMBER OF SEQUENCES: 3


(2) INFORMATION FOR SEQ ID NO: 1:

     (i) SEQUENCE CHARACTERISTICS:
          (A) LENGTH: 18 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO: 1:

GCTCCCAGGC TCAGATCT                                                    18
```

-continued

```
(2) INFORMATION FOR SEQ ID NO: 2:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO: 2:

GGTGGAGAGG CTATTCGGCT ATGA                                            24


(2) INFORMATION FOR SEQ ID NO: 3:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO: 3:

ATCCTGATCG ACAAGACCGG CTTC                                            24
```